(12) United States Patent
Thomas et al.

(10) Patent No.: US 6,448,472 B1
(45) Date of Patent: Sep. 10, 2002

(54) GENETIC AND EPIGENETIC MANIPULATION OF ABC TRANSPORTERS AND ECTOPHOSPHATASES FOR THE CONFERENCE OF HORMONE AND HERBICIDE RESISTANCE

(75) Inventors: Collin E. Thomas; J. Brian Windsor; Stan J. Roux; Alan M. Lloyd, all of Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/244,791

(22) Filed: Feb. 5, 1999

(51) Int. Cl.$^7$ .......................... C12N 15/82; C12N 5/04; C12N 15/90; A01H 5/00
(52) U.S. Cl. .................... 800/278; 435/320.1; 435/418; 435/419; 435/468; 800/298; 800/300
(58) Field of Search ......................... 435/69.1, 320.1, 435/410, 418, 419, 468; 800/278, 295, 298, 300

(56) References Cited

U.S. PATENT DOCUMENTS 5,498,533 A * 3/1996 Pooviah et al. ............. 435/468

OTHER PUBLICATIONS

Sidler et al, Plant Cell, vol. 10, pp. 1623–1636, 1998.*
Hseih et al, Plant Mol. Biol., vol. 30, pp. 135–147, 1996.*
Handa et al, Biochem. Biophysic. Res. Comm., vol. 218, pp. 916–923, 1996.*
McCabe et al, Biotechnol., vol. 6, pp. 923–926, 1988.*
Komoszynski et al, Biochimica Biophys. Acta, vol. 1310, pp. 233–241, 1996.*
Thomas et al, Plant Cell, vol. 12, pp. 519–533, 2000.*
Zielinski, R. E., Annu. Rev. Plant Physiol. Plant Mol. Biol. vol. 49, pp. 697–725, 1998.*
Lu et al. AtMRP2, An Arabidopsis ATP Binding Cassette Transporter Able to Transport Glutathione S–Conjugates and Chlorophyll Catabolites. Plant Cell. Feb. 1998, vol. 10, pp. 267–282.
Sanchez–Fernandez et al. Cloning and Expression Analyses of AtMRP4, A Novel MRP–like Gene from *Arabidopsis thaliana*. Mol. Gen. Genet. 1998, vol. 258, pp. 655–662.
Hsieh et al. Light–modulated Abundance of an mRNA Encoding a Calmodulin–regulated Chromatin–associated NTPase in Pea. Plant Mol. Biol. 1996, vol. 30, pp. 135–147.

Decottignies et al. ATPase and Multidrug Transport Activities of the Overexpressed Yeast ABC Protein Yor1p. J. Biol. Chem. May 15, 1998, vol. 273, No. 20, pp. 12612–12622.
Dudler et al. Structure of an Mdr–like Gene from *Arabidopsis thaliana*: Evolutionary Implications. J. Biol. Chem. Mar. 25, 1992, vol. 267, No. 9, pp. 5882–5888.
Grant et al. Overexpression of Multidrug Resistance–associated Protein (MRP) Increases Resistance to Natural Product Drugs. Can. Res. Jan. 15, 1994, vol. 54, pp. 357–361.
Abraham et al., 1998, *Proceedings of American Association of Cancer Research* Abstract #2575.
Pietkiewicz, J., et al., *Proc. Amer. Assoc. Canc. Res.* 39:1166.
Thomas et al., 1998, *American Society of Plant Physiologists* Abstract #649.
Abraham, E. H. et al., *Science* 275: 1324–1326.
Boyum and Guidotti, 1997, *Biochem. and Biophys. Res. Comm.* 230:22–26.
Wadkins and Roepe, 1997, *International Review of Cytology* 171:121–165.
Ujhazy et al., 1996, *Int. J. Cancer* 68:493–500.
Al–Awqati, 1995, *Science* 269:805–806.
Schweibert, 1995, *Cell* 81:1063–1073.
Ujhazy et al., 1994, *Int. . Cancer* 59:83–93.
Abraham et al., 1993, *Proc. Natl. Acad. Sci. USA* 90:312–316.
Huang et al., 1992, *Biochem. Biophys. Res. Commun.* 182:836–843.
Weiner et al., 1986, *J. Biol. Chem.* 261:4529–4534.

* cited by examiner

*Primary Examiner*—Amy J. Nelson
*Assistant Examiner*—Ashwin D. Mehta
(74) *Attorney, Agent, or Firm*—Fulbright & Jaworski LLP

(57) ABSTRACT

The present invention relates to methods for modulating the resistance of cells to foreign compounds, i.e. drugs, antibiotics, etc by altering the ATP gradient across biological membranes. The altering of the ATP gradient across biological membranes is achieved through the manipulation of ecto-phosphatase activity and ABC transporter molecule activity which may be useful to confer herbicide resistance to plants, confer antibiotic resistance to bacteria, confer drug resistance to yeast cells, or to reduce resistance in cells to facilitate chemotherapeutic treatments, and to reduce resistance in bacteria and yeast to aid in the treatment of certain infections and disease.

20 Claims, 13 Drawing Sheets

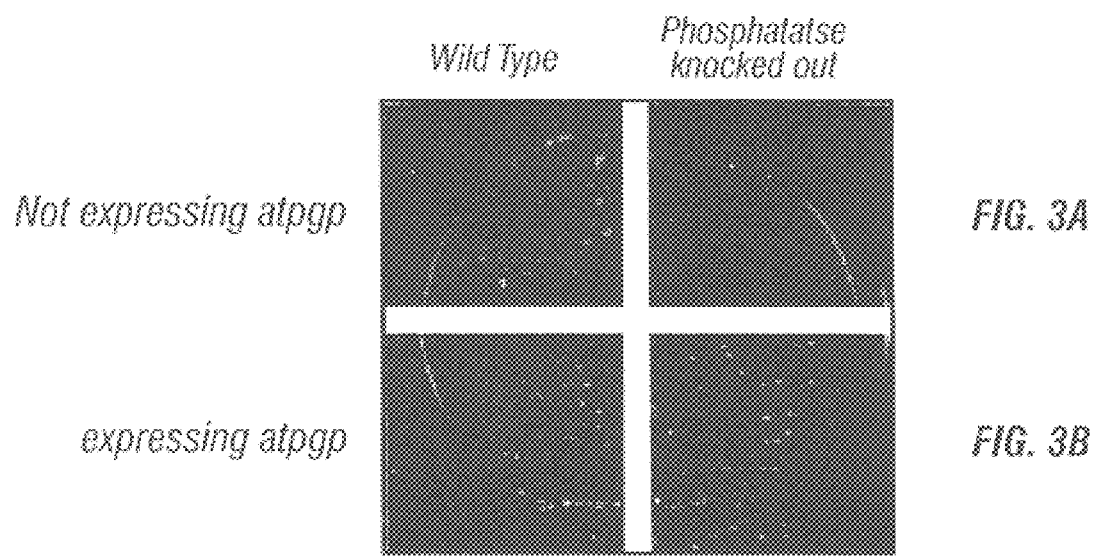
FIG. 3A
FIG. 3B
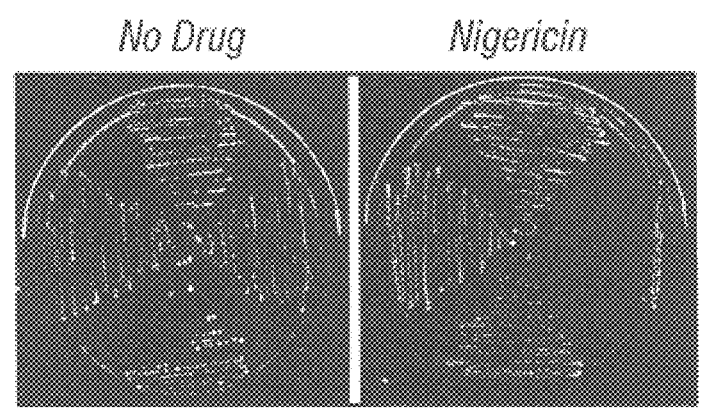
FIG. 3C
FIG. 3D

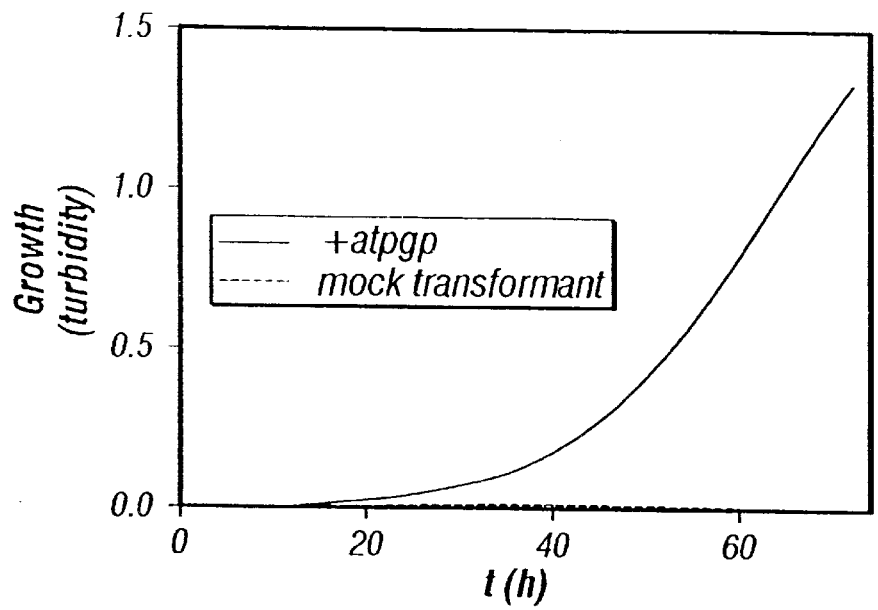
FIG. 5A
| | Day 0 | Day 1 | Growth on Nigericin Drug selected cells Day 2 | Day 3 |
|---|---|---|---|---|
| ym4mdr1 | 0 | 0.016 | 0.238 | 1.135 |
| ymr4 pvt | 0 | 0.002 | 0.001 | 0.576 |
| inv scmdr1 | 0 | 0.018 | 0.445 | 1.23 |
| inv sc pvt | 0 | 0.018 | 0.241 | 1.047 |
FIG. 5B
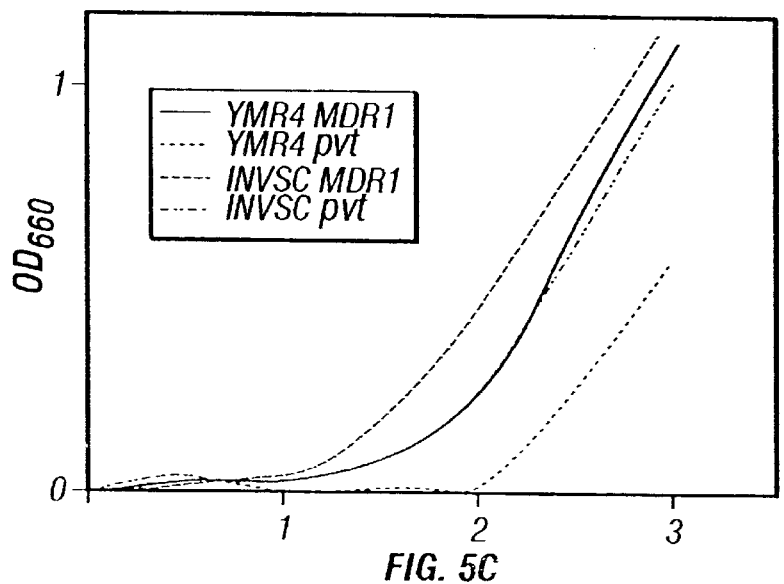
FIG. 5C

|  | Drug selected Cells | Cells cultured only on Media |
|---|---|---|
| Cycloheximide | | |
| ym4mdr1 | 0.754 | 0.014 |
| ymr4 pvt | 0.017 | 0.016 |
| inv scmdr1 | 0.683 | 0.013 |
| inv sc pvt | 0.985 | 0.005 |
| ATP+cycloheximide | | |
| ym4mdr1 | 0.001 | 0.001 |
| ymr4 pvt | 0.002 | 0.001 |
| inv scmdr1 | 0.001 | 0.002 |
| inv sc pvt | 0.001 | 0.002 |
| ATP | | |
| ym4mdr1 | 0.016 | 0.585 |
| ymr4 pvt | 0.001 | 0.697 |
| inv scmdr1 | 0.271 | 1.267 |
| inv sc pvt | 0.052 | 0.213 |
| Media alone | | |
| ym4mdr1 | 1.477 | 1.478 |
| ymr4 pvt | 1.437 | 1.484 |
| inv scmdr1 | 1.498 | 1.483 |
| inv sc pvt | 1.488 | 1.435 |

*FIG. 13*

| Media alone | | Cycloheximide | |
|---|---|---|---|
| ymr mdr1 | 1.376 | ymr mdr1 | 0.937 |
| ymr4 pvt | 1.429 | ymr4 pvt | 0.001 |

| $PQ_4$ alone | | $PQ_4$ and Cycloheximide | |
|---|---|---|---|
| ymr mdr1 | 1.351 | ymr mdr1 | 0.541 |
| ymr4 pvt | 1.341 | ymr4 pvt | 0.001 |

| Adenosine alone | | Adenosine and Cycloheximide | |
|---|---|---|---|
| ymr mdr1 | 1.319 | ymr mdr1 | 0.632 |
| ymr4 pvt | 1.354 | ymr4 pvt | 0.002 |

| Adenoside and $PQ_4$ alone | | Adenoside and $PQ_4$ and Cycloheximide | |
|---|---|---|---|
| ymr mdr1 | 0.899 | ymr mdr1 | 0.389 |
| ymr4 pvt | 1.342 | ymr4 pvt | 0.001 |

GENETIC AND EPIGENETIC MANIPULATION OF ABC TRANSPORTERS AND ECTOPHOSPHATASES FOR THE CONFERENCE OF HORMONE AND HERBICIDE RESISTANCE

The present invention involves subject matter developed under NSF Grant Numbered IBN9603884, so that the United States Government may have certain rights herein.

INTRODUCTION

The present invention is concerned with modulating the drug resistance pathways of cells in order to either confer or overcome resistance to certain drug molecules. Such modulation entails modulation of an extra-cellular phosphatase (ecto-phosphatase) and an ABC (ATP-binding cassette) transporter in order to achieve the desired effect on drug resistance. Stimulation of the ecto-phosphatase either alone or together with stimulation of the ABC transporter yields an increased resistance to drug molecules while inhibition of the ecto-phosphatase alone or together with the ABC transporter yields reduced resistance to the drug molecule. Drug resistance is achieved through the altering of the ATP gradient across biological membranes which is effectuated through the modulation of an ecto-phosphatase either alone or together with an ABC transporter molecule. Modulation of drug resistance as described herein is useful in conferring herbicide resistance to plants; conferring drug resistance to microorganisms and tissue culture cells; reducing drug resistance in tumor cells for improved chemotherapy applications; and reducing resistance to antibiotics, antifungal agents, and other drugs in microorganisms for the treatment of infections and disease.

BACKGROUND OF THE INVENTION

Transport Processes

Cells can use a phenomenon called symport to move soluble products across biological membranes. Symport is a form of coupled movement of two solutes in the same direction across a membrane by a single carrier. Examples of proton and sodium-linked symport systems are found in nearly all living systems. The energetics of the transport event depend on the relative size and electrical nature of the gradient of solutes.

Transport processes have been classified on the basis of their energy-coupling mechanisms. Currently there are four classifications: (1) Primary Active Transport which uses either a chemical, light or electrical energy source, (2) Group Translocation which uses chemical energy sources, (3) Secondary Active Transport which uses either a sodium or proton electrochemical gradient energy source, and (4) Facilitated Diffusion which does not require an energy source. Meyers, R. A., 1997, *Encyclopedia of Molecular Biology and Molecular Medicine* 6:125–133. The present invention is related to transport molecules belonging to the first class of transport processes, primary active transport, and therefore, this type of transport will be discussed in further detail.

Primary active transport refers to a process whereby a "primary" source of energy is used to drive the active accumulation of a solute into or extrusion of a solute from a cell. Transport proteins include P-type ATPases and ABC-type ATPases. These types of transport systems are found in both eukaryotes and prokaryotes. The bacterial ABC-type transporters, which are ATP-driven solute pumps, have eukaryotic counterparts. Additionally, many transmembrane solute transport proteins exhibit a common structural motif The proteins in these families consist of units or domains that pass through the membrane six times, each time as an α-helix. This has led to the suggestion that many transport proteins share a common evolutionary origin, but this is not true of several distinct families of transport proteins. Numerous structurally distinct bacterial permeases, as well as several homologous eukaryotic transport systems, share a common organization. Meyers, R. A., 1997, *Encyclopedia of Molecular Biology and Molecular Medicine* 6:125–133. Two hydrophilic domains or proteins function to couple ATP hydrolysis in the cytoplasm to activate substrate uptake or efflux, and two hydrophobic domains or proteins function as the transmembrane substrate channels. These proteins or protein domains constitute what is referred to as the ABC (ATP-binding cassette) superfamily. Either the two hydrophilic domains or proteins or the two hydrophobic domains or proteins (or both) may exist either as heterodimers or homodimers. If, as in most bacterial systems, each of these constituents is a distinct protein, then either two, three, or four genes will code for them, depending on whether both are homodimers, one is a homodimer and one is a heterodimer, or both are heterodimers, respectively. The best characterized of the eukaryotic proteins included in this family are the multidrug-resistance (MDR) transporter and the cystic fibrosis related chloride ion channel of mammalian cells (cystic fibrosis transmembrane conductance regulator or CFTR). Meyers, R. A., 1997, *Encyclopedia of Molecular Biology and Molecular Medicine* 6:125–133.

Multidrug Resistance

Multidrug resistance (MDR) is a general term that refers to the phenotype of cells or microorganisms that exhibit resistance to different, chemically dissimilar, cytotoxic compounds. MDR can develop after sequential or simultaneous exposure to various drugs. MDR can also develop before exposure to many compounds to which a cell or microorganism may be found to be resistant. MDR which develops before exposure is frequently due to a genetic event which causes the altered expression and/or mutation of an ATP-binding cassette (ABC) transporter. Wadkins, R. M. and Roepe, P. D., 1997, *International Review of Cytology* 171:121–165. This is true for both eukaryotes and prokaryotes. Id.

One prominent member of the ABC family, P-glycoprotein (Pgp; also known as multidrug resistance protein or MDR1), which is a plasma-membrane glycoprotein that confers a multidrug resistance (MDR) phenotype on cells, is of considerable interest because it provides one mechanism of possibly inhibiting resistance in tumor cells to chemotherapeutic agents. Senior, A E. et al., 1995, *FEBS Letters* 377:285–289. Pgp is a single polypeptide of ~1280 amino acids with the typical ABC transporter structure profile. Studies have shown that over-expression of Pgp is responsible for the ATP-dependent extrusion of a variety of compounds, including chemotherapeutic drugs, from cells. Abraham, E. H. et al., 1993, *Proc. Natl. Acad. Sci. USA* 90:312–316.

Over one-hundred ABC transporters have been identified in species ranging from *Escherichia coli* to humans. Higgins C. F., 1995, *Cell* 82:693–696. For example, the bacteria *Lactococcus lactis* expresses an ABC transporter, LmrA, which mediates antibiotic resistance by extruding amphiphilic compounds from the inner leaflet of the cytoplasmic membrane. van Veen H. W. et al., 1998, *Nature* 391:291–295. Furthermore, over-expression of LmrA can confer MDR in human lung fibroblasts and LmrA has similar molecular and biochemical properties to Pgp. Id. This demonstrates that bacterial LmrA and Pgp are functionally interchangeable. Id. Additionally, the plant *Arabidopsis thaliana* encodes an ATP transporter, AtPGP-1, which is a putative Pgp homolog. Dudler, R. and Hertig, C., 1992, *Journal of Biological Chemistry* 267:5882–5888. Similarly, the yeast *Saccharomyces cerevisiae* equivalent of Pgp, STS1 (Bissinger, P. H and Kucher, K., 1994, *J. Biol. Chem.* 269:4180–4186), has been cloned and shown to confer multidrug resistance when over-expressed in yeast, as has the yeast Pdr5p (Kolacskowski et al., 1996, *J. Biol. Chem.* 271:31543–31548). Taken together, these results suggest that this type of multidrug resistance efflux pump is conserved from bacteria to humans.

While various theories of ABC transporter function have become popular, there is still no precise molecular-level description for the mechanism by which over-expression lowers intracellular accumulation of drugs, in particular how Pgp lowers intracellular accumulation of chemotherapeutic drugs. However, it has been shown that Pgp over-expression also changes plasma membrane electrical potential and intracellular pH which could potentially greatly affect the cellular flux of a large number of compounds to which Pgp confers resistance. Randy M. Wadkins and Paul D. Roepe, 1997, *International Review of Cytology* 171:121–165. Also included in the ABC transporter superfamily are the Cystic Fibrosis Transmembrane Conductance Regulator (CFTR) and the Sulfonyl Urea Receptor (SUR). CFTR and SUR are expressed in the lung epithelium and the β cells of the pancreas, respectively, as well as in other tissues. CFTR functions as a low conductance ATP and cyclic AMP-dependent $Cl^-$ channel that also appears to have additional important functions, such as modulation of epithelial $Na^+$ conductance and regulation of outwardly rectified chloride channels. Wadkins, R. M. and Roepe, P. D., 1997, *International Review of Cytology* 171:121–165. Mutations in the CFTR gene produce altered CFTR proteins with defects in CFTR function, leading to profound alterations in epithelial salt transport and altered mucous properties in cystic fibrosis patients that result in chronic lung infections associated with the disease. Id. SUR is triggered by sulfonyl urea drugs to depolarize pancreatic β cells that leads to $Ca^{2+}$ influx, which stimulates fusion of insulin-containing vesicles to the plasma membrane. Id. An ATP transporter hypothesis has been suggested for Pgp, CFTR and SUR which theorizes that these ABC transporters function as ATP transport channels. Abraham, E. H. et al, 1993, *Proc. Natl. Acad. Sci. USA* 90:312–316; Schweibert, E. M., 1995, *Cell* 81:1063–1073; and Al-Awqati, Q., 1995, *Science* 269:805–806. The ATP channel hypothesis, however, has been viewed with skepticism. This is partly due to the inability to show the same results with preparations including purified and reconstituted CFTR, suggesting that the ATP conductance that was originally observed may have been mediated by another protein, not present in the purified system, that is influenced by CFTR. Wadkins, R. M. and Roepe, P. D., 1997, *International Review of Cytology* 171:121–165. There has been no such negative data reported with respect to the ATP channel hypothesis for Pgp or SUR, but the controversy over CFTR has raised doubt for Pgp and SUR as well.

In support of the ATP channel hypothesis, Huang et al. (*Biochem. Biophys. Res. Commun.* 182:836–843 (1992)) have suggested that extracellular ATP leads to elevations in pH, and Weiner et al. (*J. Biol. Chem.* 261:4529–4534 (1986)) have suggested that extracellular ATP may regulate $Na^-/H^+$ exchange in Ehrlich ascites tumor cells. It has also been observed that changes in Pgp levels affects pH and plasma membrane electrical potentials which could be connected to recent observations suggesting the involvement of ATP transport in MDR.

Additionally, Abraham et al. (*Proc. Natl. Acad. Sci. USA* 90:312–316 (1993)) have reported that the addition of extracellular ATP to MDR cell lines confers sensitivity to drugs abolishing MDR. The data for this effect were not presented in the article and no further explanation was given for this phenomenon. Furthermore, there have been no subsequent publications addressing or explaining this effect.

Furthermore, Ujhazy et al. (*Int. J. Cancer* 68:493–500 (1996)) have shown that ecto-5'-nucleotidase is up-regulated in certain MDR cell lines. Ecto-5'-nucleotidase is the final enzyme in the extracellular pathway for salvage of adenosine from phosphorylated purines. Zimmerman H., 1992, *Biochem. J.* 285:345–365. The proposed hypothesis for the involvement of ecto-5'-nucleotidase in drug resistance considers its role in the maintenance of intracellular ATP pools through the adenosine salvage pathway. Ujhazy et al., 1996, *Int. J. Cancer* 68:493–500. Ecto-5'-nucleotidase specifically acts in adenosine salvage pathways, converting AMP to adenosine which is more readily taken up by the cell and utilized as a precursor for ATP production. Therefore, ecto-5'-nucleotidase may be acting in certain MDR cell lines as a mechanism by which the cell circumvents the loss of ATP (due to up-regulated transport proteins which possibly form ATP transport channels) by creating higher levels of adenosine from which the cell can produce ATP. Correspondingly, 63% of MDR cell line variants tested expressed ecto-5'-nucleotidase. These observations suggested that a salvage mechanism for extracellular nucleotides may be another way by which certain MDR cells counterbalance their ATP losses from efflux induced by the over-expression of ABC transporters involved in MDR. Consistent with this hypothesis, inhibitors of ecto-5'-nucleotidase conferred sensitivity to certain drugs in MDR cell lines which over-express the ecto-5'-nucleotidase.

It is also interesting to note that yeast, which do not have an adenosine salvage pathway (Boyum, R. and Guidotti, G., 1997, *Microbiology* 143:1901–1908), do contain a Pgp-like gene called STS1 (Bissinger, P. H. and Kucher, K., 1994, J. Biol. Chem. 269:4180–4186. Therefore, since the adenosine salvage pathway is unlikely to be involved in yeast multidrug resistance, other mechanisms are likely to exist.

Recent reports have confirmed the existence of ATP in the extracellular matrix (ECM) of both multicellular organisms and unicellular organisms. Sedaa, K. et al., 1990, *J. Pharmacol. Exp. Ther.* 252:1060–1067 and Boyum, R. and Guidotti, G., 1997, *Microbiology* 143:1901–1908, respectively. However, no such reports are available which suggest the existence of ATP in the ECM of plants before the present invention. These reports have prompted further investigations of the fate of ATP outside the cell. One of the largest gradients in biological systems is that of ATP. It is a million-fold more concentrated inside the cell than outside. Apyrases are enzymes whose unifying characteristic is their ability to hydrolyze the gamma phosphate of ATP and to a lesser extent, the beta phosphate of ADP. Plesner, L., 1995, *Int. Rev. Cyto.* 158:141–214. Most apyrases are expressed as plasma membrane associated proteins with their hydrolytic activity facing into the ECM. Wang, T. and Guidotti, G., 1996, *J. Biol. Chem.* 271:9898–9901. Extracellular apyrases are generally referred to as ecto-apyrases. Given reports that show the existence of extracellular ATP, one observation regarding ecto-apyrase is that it hydrolyzes the extracellular ATP. In fact, work in animal systems has shown that apyrases hydrolyze ATP in the ECM as part of the adenosine salvage pathway con-jointly with ecto-5' ectonucleotidase. Che, M., 1992, *J. Biol. Chem.* 267:9684–9688. The existence of a similar ecto-apyrase system has not been reported in plants prior to the present invention. Additionally, ecto-apyrases have not been shown, prior to the present invention, to have a role in MDR.

While some references appear to indicate that MDR may act at the level of ATP transport, the role of ATP in MDR has not been adequately elucidated and has remained a point of contention in the field. The present invention provides insight into the role of ATP transport in MDR by showing that the extracellular ATP pool in cells is critical in MDR. While the adenosine salvage pathway may help compensate for ATP losses in MDR by providing a mechanism to recoup adenosine, it is not the critical aspect of the role of ATP in MDR as evidenced by the observation that only a subset of MDR cell lines resort to this mechanism via the up-regulation of ecto-5'-nucleotidase to maintain drug resistance. In fact, the previous data teach away from modulating extracelluar ATP levels and place the focus on mechanisms which are involved in modulating intracellular ATP levels. Since AMP is the preferred substrate for ecto-5'-nucleotidase, with ATP and ADP being poor substrates (Zimmerman, H., 1992, *Biochem. J.* 285:345–365), it is unlikely that ecto-5'-nucleotidase is involved in modulating extracellular levels of ATP. While high levels of ATP have been demonstrated to be useful in the inhibition of tumor growth, its effects on tumor cells have been shown to prevent cell growth and induce cell death through the inhibition of the S phase of the cell cycle. U.S. Pat. No. 4,880,918. There has been no implication, prior to the present invention, of the importance of modulating extracellular ATP levels in MDR.

It would be particularly useful to have more effective mechanisms by which to modulate drug resistance in various organisms. In particular, since the use of Pgp inhibitors has not been totally efficient in overcoming the resistance seen in tumor cells which have been repeatedly exposed to chemotherapeutic agents, it would be useful to have other mechanisms by which to combat such resistance in tumor cells to provide more effective chemotherapeutic treatments. Furthermore, there are many other applications for the modulation of drug resistance which are contemplated by the present invention, such as the engineering of herbicide resistant plants for use in agriculture.

SUMMARY OF THE INVENTION

The present invention is directed to a method for the modulation of drug resistance in cells. In one embodiment, resistance is conferred through over-expression by genetic manipulation of ABC transporters and ecto-phosphatases which are capable of affecting extracellular ATP pools and thus affecting the ATP gradient across biological membranes. Conference of resistance is useful to achieve herbicide resistance in plants, drug resistance in yeast (i.e. resistance to anti-fungal agents) in biotechnology applications, antibiotic resistance in bacteria in biotechnology applications and for drug resistance in eukaryotic tissue culture cells in biotechnology applications. In another embodiment, loss of drug resistance is achieved by suppressing the breakdown of extracellular ATP through the down-regulation of ecto-phosphatases in the presence or absence of the down-regulation of ABC transporters. Loss of resistance is useful to mitigate drug resistance problems associated with chemotherapy and in the treatment of infections from resistant strains of microorganisms. The modulation of drug resistance is achieved, at least in part, by altering the ATP gradient across biological membranes through the aforementioned manipulation of ABC transporters and ecto-phosphatases.

BRIEF DESCRIPTION OF THE FIGURES

FIG. 3A, 3B, 3C, 3D. Conference of resistance to cycloheximide (A and B) and nigericin (C and D) in wild-type and ecto-phosphatase deficient yeast over-expressing the Arabidopsis plant ABC transporter,: AtPGP-1.

FIG. 5. Graph showing the growth turbidity of YMR4 yeast over-expressing the Arabidopsis plant ABC transporter AtPGP-1 grown in cycloheximide (A) or nigericin (B and C).

FIG. 13. Growth effects of cycloheximide and extracellular ATP on wild-type and MDR1 overexpressing *S. cerevisiae* yeast cells which have either never seen cycloheximide or which have been previously selected in cycloheximide.

FIG. 14. Growth effects of cycloheximide, adenosine and phosphate on wild-type and AtPGP-1 overexpressing *S. cerevisiae* yeast cells.

DETAILED DESCRIPTION OF THE INVENTION

Figure 1A:
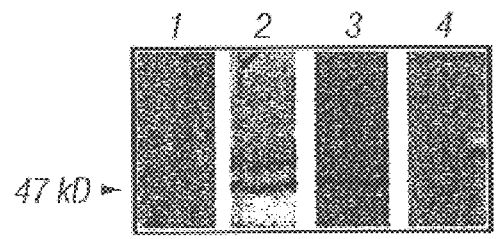
FIG. 1A, 1B, 1C. Expression of apyrase in pea and in transgenic plants (A) Immunoblot analysis of subcellular fractions from etiolated pea plants. (B) Top, the total phosphate accumulated in the shoots of three independent transgenic plants. Bottom, a corresponding immunoblot performed on protein from ECM of wild-type and transgenic plants. (C) Assay of phosphatase activity in the ECM fraction of OE1 and wild-type.

For purposes of clarity of description, and not by way of limitation, the detailed description of the invention is divided into the following subsections:

(i) conference of herbicide resistance in plants;
(ii) conference of drug resistance in recombinant research applications;
(iii) inhibition of drug resistance in chemotherapy;
(iv) inhibition of drug resistance in microorganisms to treat infection;

Conference of Herbicide Resistance in Plants

The present invention is directed to a method for the modulation of drug resistance in plants, particularly herbicide resistance, in part through the manipulation of the ATP gradient across biological membranes. In accordance with the invention, the manipulation of extracellular ATP levels and hence the ATP gradient across biological membranes in plant cells by the over-expression of a MDR-ABC transporter and an ecto-phosphatase, results in resistance to certain plant hormones, drugs and herbicides. Such resistance is useful in horticulture of recombinant crops for the elimination of other unwanted plants (e.g. weeds) which are not resistant. The invention is based, in part, on the unexpected observation that the over-expression of either an ecto-phosphatase, or an ABC transporter can confer resistance to certain drugs and herbicides in plants.

Up-regulation as used herein refers to increasing the activity of a molecule within a cell by either providing an outside source of the molecule (e.g. an expression cassette containing a DNA encoding the molecule) either in single copy or multiple copies which when expressed in the cell increases the amount of the molecule in the cell, by increasing the transcription of the endogenous or exogenous molecule to increase the amount of the molecule in the cell, or by modifying the exogenous or endogenous molecule in the cell post-translationally to achieve an increase in activity of the molecule. Down-regulation as used herein refers to decreasing the activity of a molecule in a cell by either decreasing the amount of the molecule in the cell (this may be achieved by over-expression of an anti-sense RNA corresponding to the molecule or by inhibiting factors necessary for the expression of the molecule) or by modifying the exogenous or endogenous molecule in the cell post-translationally to achieve a decrease in activity. Such post translational modifications may include phosphorylation, adenylation, glycosylation, ubiquitinylation, acetylation, methylation, farnesylation, myristilation and sulfation.

The ecto-phosphatases remove phosphate from any ATP extruded from the cell, rendering the ATP ineffectual for transport of drugs back into the cell. Ecto-phosphatases as referred to herein do not include extracellular phosphatases involved in the adenosine salvage pathway. MDR ABC transporters form channels which facilitate the efflux of molecules, including drugs, from cells. This efflux is likely effectuated through the "piggy-back" efflux of drug molecules with ATP, a phenomenon known as symport.

In one embodiment of the invention, the over-expression of an ecto-phosphatase confers drug resistance in both wild-type and/or genetically engineered plants. This effect is seen in plant cells over-expressing plant apyrase grown in the presence of (1) cycloheximide, a potent inhibitor of protein expression, (2) nigericin, an antibiotic which effects ion transport, and (3) $N_6$ (2-isopentenyl) adenine, a cytokinin plant hormone which is herbicidal at micromolar and millimolar concentrations.

In another embodiment of the invention, the over-expression of an ABC transporter confers drug resistance in wild-type and genetically engineered plants. In a preferred embodiment, the ABC transporter which is over-expressed is the Arabidopsis ABC transporter AtPGP-1. The over-expression of AtPGP-1 can confer resistance in plants to cycloheximide, nigericin and cytokinins.

In a preferred embodiment of the invention the effect of over-expression of both an MDR-ABC transporter and an ecto-phosphatase is enhancement of the ATP gradient across biological membranes and thus stimulation of resistance to certain plant hormones and herbicides. In a particularly preferred embodiment of the invention, the MDR-ABC transporter which is over-expressed is the Arabidopsis AtPGP-1 and the ecto-phosphatase that is over-expressed is apyrase.

The invention particularly contemplates the conference of resistance in plants to herbicides which resemble established drugs implicated in multidrug resistance, as well as plant hormones such as cytokinin, auxins, gibberellins and brassinosteroids. The present invention also contemplates the conference of resistance in plants to the nonlimiting list of chemicals, such as those set forth in Table 1*.

TABLE 1

| Common Name | Chemical Name |
| --- | --- |
| acetochlor | chloro-N-(ethoxymethyl)-N-(2-ethyl-6-methyl-phenyl)acetamide |
| acifluorfen | 5-[2-chloro-4-(trifluoromethyl)phenoxy]-2-nitro-benzoic acid |
| acrolein | 2-propenal |
| alachlor | 2-chloro-N-(2,6-diethylphenyl)-N-(methoxy-methyl)acetamide |
| allyl alcohol | 2-propen-1-ol |
| ametryn | N-ethyl-N'-(1-methylethyl)-6-(methyl-thio)-1,3,5-triazine-2,4-diamine |
| amitrole | 1H-1,2,4-triazol-3-amine |
| AMS | ammonium sulfamate |
| arsenic acid | arsenic acid |
| asulam | methyl[(4-aminophenyl)sulfonyl]carbamate |
| atraton | N-ethyl-6-methoxy-N'-(1-methylethyl)-1,3,5-tri-azine-2,4-diamine |
| atrazine | 6-chloro-N-ethyl-N'-(1-methylethyl)-1,3,5-tri-azine-2,4-diamine |
| azafenidin | 2-[2,4-dichloro-5-(2-propynyloxy)phe-nyl]-5,6,7,8-tetrahydro-1,2,4-tri-azolo[4,3-a]pyridin-3(2H)-one |
| azimsulfuron | N-[[(4,6-dimethoxy-2-pyrimidinyl)ami-no]carbonyl]-1-methyl-4-(2-methyl-2H-tetrazol-5-yl)-1H-pyrazole-5-sulfonamide |
| barban | 4-chloro-2-butynyl 3-chlorophenylcarbamate |
| BCPC | 1-methylpropyl 3-chlorophenylcarbamate |
| benazolin | 4-chloro-2-oxo-3(2H)-benzothiazoleacetic acid |
| benefin | N-butyl-N-ethyl-2,6-dinitro-4-(tri-fluoromethyl)benzenamine |
| bensulfuron | 2-[[[[(4,6-dimethoxy-2-pyri-midinyl)amino]carbonyl]amino]sulfonyl]methyl]benzoic acid |
| bensulide | O,O-bis(1-methylethyl)S-[2-[(phenyl-sulfonyl)amino]ethyl]phosphorodithioate |
| bentazon | 3-(1-methylethyl)-(1H)-2,1,3-benzo-thiadiazin-4(3H)-one 2,2-dioxide |
| benzadox | [(benzoylamino)oxy]acetic acid |
| benzipram | 3,5-dimethyl-N-(1-methylethyl)-N-(phenyl-methyl)benzamide |
| benzofluor | N-[4-(ethylthio)-2-(trifluoro-methyl)phenyl]methanesulfonamide |
| benzoylprop | N-benzoyl-N-(3,4-dichlorophenyl)-DL-alanine |
| benzthiazuron | N-2-benzothiazolyl-N'-methylurea |
| bifenox | methyl 5-(2,4-dichlorophenoxy)-2-nitrobenzoate |
| borax | sodium tetraborate |
| bromacil | 5-bromo-6-methyl-3-(1-methyl-propyl)-2,4(1H, 3H)pyrimidinedione |
| bromofenoxim | 3,5-dibromo-4-hydroxybenzaldehyde O-(2,4-dinitrophenyl)oxime |
| bromoxynil | 3,5-dibromo-4-hydroxybenzonitrile |
| butachlor | N-(butoxymethyl)-2-chloro-N-(2,6-diethyl-phenyl)acetamide |

TABLE 1-continued

| Common Name | Chemical Name |
|---|---|
| butam | 2,2-dimethyl-N-(1-methylethyl)-N-phenyl-methyl)propanamide |
| butamifos | O-ethyl O-(5-methyl-2-nitrophenyl) 1-methylpropylphosphoramidothioate |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methyl-propyl)-2,6-dinitrobenzenamine |
| buturon | N'-(4-chlorophenyl)-N-methyl-N-(1-methyl-2-propynyl)urea |
| butylate | S-ethyl bis(2-methylpropyl)carbamothioate |
| cacodylic acid | dimethyl arsinic acid |
| cambendichlor | (phenylimino)di-2,1-ethanediyl bis(3,6-di-chloro-2-methoxybenzoate) |
| carbetamide | N-ethyl-2-[[(phenylamino)carbonyl]oxy]pro-panamide (R)-isomer |
| CDAA | 2-chloro-N,N-di-2-propenylacetamide |
| carfentrazone | "the alpha character", 2-dichloro-5-[4-(difluoromethyl)-4,5-di-hydro-3-methyl-5-oxo-1H-1,2,4-tria-zol-1-yl]-4-fluorobenzenepropanoic acid |
| CDEA | 2-chloro-N,N-diethylacetamide |
| CDEC | 2-chloro-2-propenyl diethylcarbamodithioate |
| CEPC | 2-chloroethyl (3-chlorophenyl)carbamate |
| chloramben | 3-amino-2,5-dichlorobenzoic acid |
| chlorazine | 6-chloro-N,N,N',N'-tetraethyl-1,3,5-tri-azine-2,4-diamine |
| chlorbromuron | N'-(4-bromo-3-chlorophenyl)-N-me-thoxy-N-methylurea |
| chlorbufam | 1-methyl-2-propynyl (3-chlorophenyl)carbamate |
| chlorflurenol | 2-chloro-9-hydroxy-9H-fluorene-9-car-boxylic acid |
| chlorimuron | 2-[[[[(4-chloro-6-methoxy-2-pyrimidinyl)ami-no]carbonyl]amino]sulfonyl]benzoic acid |
| chloroxuron | N'-[4-(4-chlorophenoxy)phe-nyl]-N,N-dimethylurea |
| chlorpropham | 1-methylethyl 3-chlorophenylcarbamate |
| chlorsulfuron | 2-chloro-N-[[(4-methoxy-6-methyl-1,3,5-tri-azin-2-yl)amino]carbonyl]benzenesulfonamide |
| chlorthiamid | 2,6-dichlorobenzenecarbothiamide |
| chlortoluron | N'-(3-chloro-4-methylphenyl)-N,N-dimethylurea |
| cinmethylin | exo-(±)-1-methyl-4-(1-methylethyl)-2-[(2-methyl-phenyl)methoxy]-7-oxabicyclo[2.2.1]heptane |
| cisanilide | cis-2,5-dimethyl-N-phenyl-1-pyr-rolidinecarboxamide |
| clethodim | (E,E)-(±)-2-[1-[[(3-chloro-2-propenyl)oxy]imino]propyl]-5-[2-(ethylthio)pro-pyl]-3-hydroxy-2-cyclohexen-1-one |
| clofop | 2-[4-(4-chlorophenoxy)phenoxy]propanoic acid |
| clomazone | 2-[(2-chlorophenyl)methyl]-4,4-di-methyl-3-isoxazolidinone |
| cloproxydim | (E,E)-2-[1-[[(3-chloro-2-pro-penyl)oxy]imino]butyl]-5-[2-(ethyl-thio)propyl]-3-hydroxy-2-cyclohexen-1-one |
| cloransulam | 3-chloro-2-[[(5-ethoxy-7-fluoro[1,2,4]tri-azolo[1,5-c]pyrimidin-2yl)sul-fonyl]amino]benzoic acid |
| clopyralid | 3,6-dichloro-2-pyridinecarboxylic acid |
| CMA | calcium salt of MAA |
| copper sulfate | copper sulfate |
| 4-CPA | (4-chlorophenoxy)acetic acid |
| 4-CPB | 4-(4-chlorophenoxy)butyric acid |
| CPMF | 1-chloro-N'-(3,4-dichlorophenyl)-N—N-di-methylformamidine |
| 4-CPP | 2-(4-chlorophenoxy)propionic acid |
| CPPC | 2-chloro-1-methylethyl (3-chloro-phenyl)carbamate |
| cyanazine | 2-[[4-chloro-6-(ethylamino)-1,3,5-tri-azin-2-yl]amino]-2-methylpropanenitrile |
| cycloate | S-ethyl cyclohexylethylcarbamothioate |
| cyclosulfamuron | N-[[[2-(cyclopropylcarbonyl)phenyl]amino]sul-fonyl]-N'-(4,6-dimethoxy-2-pyrimidinyl)urea |
| cycluron | N'-cyclooctyl-N,N-dimethylurea |
| cyhalofop | (R)-2-[4-(4-cyano-2-fluoro-phenoxy)phenoxy]pro-panoic acid |

TABLE 1-continued

| Common Name | Chemical Name |
|---|---|
| cyperquat | 1-methyl-4-phenylpyridinium |
| cyprazine | 6-chloro-N-cyclopropyl-N'-(1-methyl-ethyl)-1,3,5-triazine-2,4-diamine |
| cyprazole | N-[5-(2-chloro-1,1-dimethylethyl)-1,3,4-thi-adiazol-2-yl]cyclopropanecarboxamide |
| cypromid | N-(3,4-dichlorophenyl)cyclopropanecarboxamide |
| 2,4-D | (2,4-dichlorophenoxy)acetic acid |
| 3,4-DA | (3,4-dichlorophenoxy)acetic acid |
| dalapon | 2,2-dichloropropanoic acid |
| dazomet | tetrahydro-3,5-dimethyl-2H-1,3,5-thi-adiazine-2-thione |
| 2,4-DB | 4-(2,4-dichlorophenoxy)butanoic acid |
| 3,4-DB | 4-(3,4-dichlorophenoxy)butanoic acid |
| DCB | 1,2-dichlorobenzene |
| DCPA | dimethyl 2,3,5,6-tetrachloro-1,4-benzene-dicarboxylate |
| DCU | N,N'-bis(2,2,2-trichloro-1-hydroxyethyl)urea |
| 2,4-DEB | 2-(2,4-dichlorophenoxy)ethyl benzoate |
| delachlor | 2-chloro-N-(2,6-dimethylphenyl)-N-[(2-methyl-propoxy)methyl]acetamide |
| 2,4-DEP | tris[2-(2,4-dichlorophenoxy)ethyl]phosphite |
| desmedipham | ethyl 3-[[(phenylamino)car-bonyl]oxy]phenyl]carbamate |
| desmetryn | N-methyl-N'-(1-methylethyl)-6-(methyl-thio)-1,3,5-triazine-2,4-diamine |
| diallate | S-(2,3-dichloro-2-propenyl) bis(1-methyl-ethyl)carbamothioate |
| dicamba | 3,6-dichloro-2-methoxybenzoic acid |
| dichlobenil | 2,6-dichlorobenzonitrile |
| dichlormate | 3,4-dichloro benzenemethanol methylcarbamate |
| dichlorprop | (±)-2-(2,4-dichlorophenoxy)propanoic acid |
| diclofop | (±)-2-[4-(2,4-dichlorophenoxy)phe-noxy]propanoic acid |
| dicryl | N-(3,4-dichlorophenyl)-2-methyl-2-propenamide |
| diethatyl | N-(chloroacetyl)-N-(2,6-diethylphenyl)glycine |
| diclosulam | N-(2,6-dichlorophenyl)-5-ethoxy-7-fluoro[1,2,4]triazolo[1,5-c]pyrimidine-2-sulfonamide |
| difenopenten | (E)-(±)-4-[4-[4-(trifluoromethyl)phe-noxy]phenoxy]-2-pentenoic acid |
| difenoxuron | N'-[4-(4-methoxyphenoxy)phe-nyl]-N,N-dimethylurea |
| difenzoquat | 1,2-dimethyl-3,5-diphenyl-1H-pyrazolium |
| dimethachlor | 2-chloro-N-(2,6-dimethylphenyl)-N-(2-methoxy-ethyl)acetamide |
| dimethametryn | N-(1,2-dimethylpropyl)-N'-ethyl-6-(methylthio)-1,3,5-triazine-2,4-diamine |
| dinitramine | N3,N3-diethyl-2,4-dinitro-6-(trifluoro-methyl)-1,3-benzenediamine |
| dinosam | 2-(1-methylbutyl)-4,6-dinitrophenol |
| dinoseb | 2-(1-methlpropyl)-4,6-dinitrophenol |
| dinoterb | 2-(1,1-dimethylethyl)-4,6-dinitrophenol |
| diphenamid | N,N-dimethyl-a-phenyl benzeneacetamide |
| dipropetryn | 6-(ethylthio)-N,N'-bis(1-methyl-ethyl)-1,3,5-triazine-2,4-diamine |
| diquat | 6,7-dihydrodipyrido[1,2-a:2',1'-c[pyra-zinediium ion |
| dithiopyr | S,S-dimethyl 2-(difluoromethyl)-4-(2-methyl-propyl)-6-(trifluoromethyl)-3,5-pyridine-dicarbothioate |
| diuron | N'-(3,4-dichlorophenyl)-N,N-dimethylurea |
| DNOC | 2-methyl-4,6-dinitrophenol |
| 3,4-DP | 2-(3,4-dichlorophenoxy) propanoic acid |
| DSMA | disodium salt of MAA |
| EBEP | ethyl bis (2-ethylhexyl)phosphinate |
| eglinazine | N-(4-chloro-6-ethylamino-1,3,5-tri-azin-2-yl)glycine |
| endothall | 7-oxabicyclo[2.2.1]heptane-2,3-dicarboxylic acid |
| endothal-sodium | Sodium salt of endothal |
| EPTC | S-ethyl dipropyl carbamothioate |
| erbon | 2-(2,4,5-trichlorophenoxy)ethyl-2,2-di-chloropropanoate |
| ethalfluralin | N-ethyl-N-(2-methyl-2-propenyl)-2,6-dini-tro-4-(trifluoromethyl)benzenamine |
| ethametsulfuron | 2-[[[[(4-ethoxy-6-(methylamino)-1,3,5-tri-azin-2-yl]amino]carbonyl]amino]sul-fonyl]benzoic acid |

TABLE 1-continued

| Common Name | Chemical Name |
|---|---|
| ethidimuron | N-(5-ethylsulfonyl-1,3,4-thiadi-azol-2-yl)-N,N'-dimethylurea |
| ethiolate | S-ethyl diethylcarbamothioate |
| ethofumesate | (±)-2-ethoxy-2,3-dihydro-3,3-dimethyl-5-benzo-furanyl methanesulfonate |
| EXD | diethyl thioperoxydicarbonate |
| fenac | 2,3,6-trichlorobenzeneacetic acid |
| fenoxaprop | (±)-2-[4-[(6-chloro-2-benzoxazolyl)oxy]phe-noxy]propanoic acid |
| fenuron | N,N-dimethyl-N'-phenylurea |
| fenuron TCA | salt of fenuron and TCA |
| flamprop | N-benzoyl-N-(3-chloro-4-fluoro-phenyl)-DL-alanine |
| fluazifop | (±)-2-[4-[[5-(trifluoromethyl)-2-pyri-dinyl]oxy]phenoxy]propanoic acid |
| fluazifop-P | (R)-2-[4-[[5-(trifluoromethyl)-2-pyri-dinyl]oxy]phenoxy]propanoic acid |
| fluchloralin | N-(2-chloroethyl)-2,6-dinitro-N-propyl-4-(tri-fluoromethyl)benzenamine |
| flumetsulam | N-(2,6-difluorophenyl)-5-methyl[1,2,4]tri-azolo[1,5-a]pyrimidine-2-sulfonamide |
| flumiclorac | [2-chloro-4-fluoro-5-(1,3,4,5,6,7-hexa-hydro-1,3-dioxo-2H-isoindol-2-yl)phe-noxy]acetic acid |
| flumioxazin | 2-[7-fluoro-3,4-dihydro-3-oxo-4-(2-pro-pynyl)-2H-1,4-benzoxazin-6-yl]-4,5,6,7-tetra-hydro-1H-isoindole-1,3(2H)-dione |
| fluometuron | N,N-dimethyl-N'-[3-(trifluoromethyl)phenyl]urea |
| fluorochloridone | 3-chloro-4-(chloromethyl)-1-[3-(trifluoro-methyl)phenyl]-2-pyrrolidinone |
| fluorodifen | 2-nitro-1-(4-nitrophenoxy)-4-trifluoro-methylbenzene |
| fluoroglycofen | carboxymethyl 5-[2-chloro-4-(trifluoro-methyl)phenoxy]-2-nitrobenzoate |
| flupropacil | 1-methylethyl 2-chloro-5-[3,6-dihydro-3-me-thyl-2,6-dioxo-4-(trifluoromethyl)-1(2H)-pyrimidinyl]benzoate |
| flupyrsulfuron | 2-[[[[(4,6-dimethoxy-2-pyrimidinyl)ami-no]carbonyl]amino]sulfonyl]-6-(trifluoro-methyl)-3-pyridinecarboxylic acid |
| fluridone | 1-methyl-3-phenyl-5-[3-(trifluoro-methyl)phenyl]-4(1H)-pyridinone |
| fluroxypyr | [(4-amino-3,5-dichloro-6-fluoro-2-pyri-dinyl)oxy]acetic acid |
| flurtamone | (±)5(methylamino)2-phenyl-4-[3-(trifluoro-methyl)phenyl]-3(2H)-furanone |
| fomesafen | 5-[2-chloro-4-(trifluoromethyl)phenoxy]-N-(methylsulfonyl)-2-nitrobenzamide |
| fosamine | ethyl hydrogen (aminocarbonyl)phosphonate |
| glufosinate | 2-amino-4-(hydroxymethylphosphinyl)bu-tanoic acid |
| glyphosate | N-(phosphonomethyl)glycine |
| halosafen | 5-[2-chloro-6-fluoro-4-(trifluoromethyl)phenoxy]-N-(ethylsulfonyl)-2-nitrobenzamide |
| haloxyfop | (±)-2-[4-[[3-chloro-5-(trifluoromethyl)-2-pyri-dinyl]oxy]phenoxy]propanoic acid |
| hexaflurate | potassium hexafluoroarsenate |
| hexazinone | 3-cyclohexyl-6(dimethylamino)-1-methyl-1,3,5-triazine-2,4(1H,3H)-dione |
| imazamethabenz | (±)-2-[4,5-dihydro-4-methyl-4-(1-methylethyl)-5-oxo-1H-imidazol-2-yl]-4(and 5)-methyl-benzoic acid (3:2) |
| imazamox | 2-[4,5-dihydro-4-methyl-4-(1-methyl-ethyl)-5-oxo-1H-imidazol-2-yl]-5-(meth-oxymethyl)-3-pyridinecarboxylic acid |
| imazapyr | (±)-2-[4,5-dihydro-4-methyl-4-(1-methyl-ethyl)-5-oxo-1H-imidazol-2-yl]-3-pyri-dinecarboxylic acid |
| imazaquin | 2-[4,5-dihydro-4-methyl-4-(1-methyl-ethyl)-5-oxo-1H-imidazol-2-yl]-3-quinolinecarboxylic acid |
| imazethapyr | 2-[4,5-dihydro-4-methyl-4-(1-methyl-ethyl)-5-oxo-1H-imidazol-2-yl]-5-ethyl-3-pyridinecarboxylic acid |
| ioxynil | 4-hydroxy-3,5-diiodobenzonitrile |
| ipazine | 6-chloro-N,N-diethyl-N'-(1-methyl-ethyl)-1,3,5-triazine-2,4-diamine |
| IPX | O-(1-methylethyl)carbonodithioate |
| isocarbamid | N-(2-methylpropyl)-2-oxo-1-imidazolidine carboxamide |
| isocil | 5-bromo-6-methyl-3-(1-methyl-ethyl)-2,4(1H,3H)-pyrimidinedione |
| isomethiozin | 6-(1,1-dimethylethyl)-4-[(2-methylpro-pylidene)amino]-3-(methylthio)-1,2,4-tri-azin-5-(4H)-one |
| isopropalin | 4-(1-methylethyl)-2,6-dinitro-N,N-di-propylbenzenamine |
| isoproturon | N,N-dimethyl-N'-[4-(1-methylethyl)phenyl]urea |
| isouron | N'-[5-(1,1-dimethylethyl)-3-isox-azolyl]-N,N-dimethylurea |
| isoxaben | N-[3-(1-ethyl-1-methylpropyl)-5-isox-azolyl]-2,6-dimethoxybenzamide |
| karbutilate | 3-[[(dimethylamino)carbonyl]amino]phenyl (1,1-dimethylethyl)carbamate |
| KOCN | potassium cyanate |
| lactofen | (±)-2-ethoxy-1-methyl-2-oxoethyl 5-[2-chloro-4-(trifluoromethyl)phe-noxy]-2-nitrobenzoate |
| lenacil | 3-cyclohexyl-6,7-dihydro-1H-cyclopenta-pyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| maleic hydrazide | 1,2-dihydro-3,6-pyridazinedione |
| MCPA | (4-chloro-2-methylphenoxy)acetic acid |
| MCPB | 4-(4-chloro-2-methylphenoxy)butanoic acid |
| mecoprop | (±)-2-(4-chloro-2-methylphenoxy)propanoic acid |
| mefluidide | N-[2,4-dimethyl-5-[[(trifluoromethyl)sul-fonyl]amino]phenyl]acetamide |
| metam-sodium | Sodium salt of metham |
| metamitron | 4-amino-3-methyl-6-phenyl-1,2,4-tri-azin-5(4H)-one |
| methalpropalin | N-(2-methyl-2-propenyl)-2,6-dinitro-N-pro-pyl-4-(trifluoromethyl)benzenamine |
| metham | methylcarbamodithioic acid |
| methazole | 2-(3,4-dichlorophenyl)-4-methyl-1,2,4-oxa-diazolidine-3,5-dione |
| methibenzuron | N-(2-benzothiazolyl-N,N'-dimethylurea |
| | N-(3-methoxypropyl)-N'-(1-methylethyl)-6-(methylthio)-methoprotryn 1,3,5-tri-azine-2,4-diamine |
| methyl bromide | bromomethane |
| metobromuron | N'-(4-bromophenyl)-N-methoxy-N-methylurea |
| | (2-methoxy-1-methylethyl)acetamide |
| metolachlor | 2-chloro-N-(2-ethyl-6-methylphenyl)-N- |
| metosulam | N-(2,6-dichloro-3-methylphenyl)-5,7-dimeth-oxy[1,2,4]triazolo[1,5-a]pyri-midine-2-sulfonamide |
| metoxuron | N'-(3-chloro-4-methoxyphenyl)-N,N-di-methyl urea |
| metribuzin | 4-amino-6-(1,1-dimethylethyl)-3-(methyl-thio)-1,2,4-triazin-5(4H)-one |
| metsulfuron | 2-[[[[(4-methoxy-6-methyl-1,3,5-tri-azin-2-yl)amino]carbonyl]amino]sul-fonyl]benzoic acid |
| molinate | S-ethyl hexahydro-1H-azepine-1-carbothioate |
| monalide | N-(4-chlorophenyl)-2,2-dimethylpentanamide |
| monolinuron | N'-(4-chlorophenyl)-N-methoxy-N-methylurea |
| monuron | N'-(4-chlorophenyl)-N,N-dimethylurea |
| monuron TCA | salt of monuron and TCA |
| MSMA | monosodium salt of MAA |
| napropamide | N,N-diethyl-2-(1-naphthalenyloxy)propanamide |
| naptalam | 2-[(1-naphthalenylamino)carbonyl]benzoic acid |
| neburon | N-butyl-N'-(3,4-dichlorophenyl)-N-methylurea |
| nicosulfuron | 2-[[[[(4,6-dimethoxy-2-pyrimidinyl)amino]car-bonyl]amino]sulfonyl]-N,N-dimethyl-3-pyri-dinecarboxamide |
| nitralin | 4-(methylsulfonyl)-2,6-dinitro-N,N-di-propylbenzenamine |
| nitrofen | 2,4-dichloro-1-(4-nitrophenoxy)benzene |
| nitrofluorfen | 2-chloro-1-(4-nitrophenoxy)-4-(trifluoro-methyl)benzene |
| norea | N,N-dimethyl-N'-(octahydro-4,7-meth-ano-1H-inden-5-yl)urea 3aa,4a,5a,7a,7aa-isomer |

TABLE 1-continued

| Common Name | Chemical Name |
|---|---|
| norflurazon | 4-chloro-5-(methylamino)-2-(3-(trifluoromethyl)phenyl)-3(2H)-pyridazinone |
| OCH | 2,3,4,4,5,5,6,6-octachloro-2-cyclohexen-1-one |
| oryzalin | 4-(dipropylamino)-3,5-dinitrobenzenesulfonamide |
| oxadiazon | 3-[2,4-dichloro-5-(1-methylethoxy)phenyl]-5-(1,1-dimethylethyl)-1,3,4-oxadiazol-2-(3H)-one |
| oxyfluorfen | 2-chloro-1-(3-ethoxy-4-nitrophenoxy)-4-(trifluoromethyl)benzene |
| paraquat | 1,1'-dimethyl-4,4'-bipyridinium ion |
| PBA | chlorinated benzoic acid |
| PCP | pentachlorophenol |
| pebulate | S-propyl butylethylcarbamothioate |
| pelargonic acid | nonanoic acid |
| pendimethalin | N-(1-ethylpropyl)-3,4-dimethyl-2,6-dinitrobenzenamine |
| perfluidone | 1,1,1-trifluoro-N[2-methyl-4-phenylsulfonyl)phenyl]methanesulfonamide |
| phenisopham | 3-[[(1-methylethoxy)carbonyl]amino]phenyl ethylphenylcarbamate |
| phenmedipham | 3-[(methoxycarbonyl)amino]phenyl (3-methylphenyl)carbamate |
| picloram | 4-amino-3,5,6-trichloro-2-pyridinecarboxylic acid |
| piperophos | S-[2-(2-methyl-1-piperidinyl)-2-oxoethyl]O,O-dipropylphosphorodithioate |
| PMA | (acetato-O)phenylmercury |
| potassium azide | potassium azide |
| primisulfuron | 2-[[[[(4,6-bis(difluoromethoxy)-2-pyrimidinyl]amino]carbonyl]amino]sulfonyl]benzoic acid |
| procyazine | 2-[[4-chloro-6-(cyclopropylamino)-1,3,5-triazine-2-yl]amino]-2-methylpropanenitrile |
| prodiamine | 2,4 dinitro-N3,N3-dipropyl-6-(trifluoromethyl)-1,3-benzenediamine |
| profluralin | N-(cyclopropylmethyl)-2,6-dinitro-N-propyl-4-(trifluoromethyl)benzenamine |
| proglinazine | N-[4-chloro-6-(1-methylethylamino)-1,3,5-triazine-2-yl]glycine |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro (N-1,1-dimethyl-2-propynyl)benzamide |
| propachlor | 2-chloro-N-(1-methylethyl)-N-phenylacetamide |
| propanil | N-(3,4-dichlorophenyl)propanamide |
| propaquizafop | (R)-2-[[(1-methylethylidene)amino]oxy]ethyl 2-[4-[(6-chloro-2-quinoxalinyl)oxy]phenoxy]propanoate |
| propazine | 6-chloro-N,N'-bis(1-methylethyl)-1,3,5-triazine-2,4-diamine |
| propham | 1-methylethyl phenylcarbamate |
| prosulfalin | N-[[4-(dipropylamino)-3,5-dinitrophenyl]sulfonyl]-S,S-dimethylsulfilimine |
| proxan-sodium | sodium salt of IPX |
| prynachlor | 2-chloro-N-(1-methyl-2-propynyl)-N-phenylacetamide |
| pyrazon | 5-amino-4-chloro-2-phenyl-3(2H)-pyridazinone |
| pyriclor | 2,3,5-trichloro-4-pyridinol |
| pyridate | O-(6-chloro-3-phenyl-4-pyridazinyl) S-octyl carbonothioate |
| pyrithiobac | 2-chloro-6-[(4,6-dimethoxy-2-pyrimidinyl)thio]benzoic acid |
| quinchlorac | 3,7-dichloro-8-quinolinecarboxlic acid |
| quinonamid | 2,2-dichloro-N-(3-chloro-1,4-dihydro-1,4-dioxo-2-naphthalenyl)acetamide |
| quizalofop | (±)-2-[4-[(6-chloro-2-quinoxalinyl)oxy]phenoxy]propanoic acid |
| rimsulfuron | N-[[(4,6-dimethoxy-2-pyrimidinyl)amino]carbonyl]-3 -(ethylsulfonyl)-2-pyridinesulfonamide |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| sesone | 2-(2,4-dichlorophenoxy)ethyl hydrogen sulfate |
| siduron | N-(2-methylcyclohexyl)-N'-phenylurea |
| silvex | 2-(2,4,5-trichlorophenoxy)propanoic acid |
| simazine | 6-chloro-N,N'-diethyl-1,3,5-triazine-2,4-diamine |
| simeton | N,N'-diethyl-6-methoxy-1,3,5-triazine-2,4-diamine |
| simetryn | N,N'-diethyl-6-(methylthio)-1,3,5-triazine-2,4-diamine |
| sodium arsenite | sodium arsenite |
| sodium azide | sodium azide |
| sodium chlorate | sodium chlorate |
| solan | N-(3-chloro-4-methylphenyl)-2-methylpentanamide |
| sulfentrazone | N-[2,4-dichloro-5-[4-(difluoromethyl)-4,5-dihydro-3-methyl-5-oxo-1H-1,2,4-triazol-1-yl]phenyl]methanesulfonamide |
| sulfometuron | 2-[[[[(4,6-dimethyl-2-pyrimidinyl)amino]carbonyl]amino]sulfonyl]benzoic acid |
| swep | methyl(3,4-dichlorophenyl)carbamate |
| 2,4,5-T | (2,4,5-trichlorophenoxy)acetic acid |
| 2,4,5-TB | 4-(2,4,5-trichlorophenoxy)butanoic acid |
| 2,3,6-TBA | 2,3,6-trichlorobenzoic acid |
| TCA | trichloroacetic acid |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]acetamide |
| terbumeton | N-(1,1-dimethylethyl)-N'-ethyl-6-methoxy-1,3,5-triazine-2,4-diamine |
| terbuthylazine | 6-chloro-N-(1,1-dimethylethyl)-N'-ethyl-1,3,5-triazine-2,4-diamine |
| terbutol | 2,6-bis(1,1-dimethylethyl)-4-methylphenyl methylcarbamate |
| terbutryn | N-(1,1-dimethylethyl)-N'-ethyl-6-(methylthio)-1,3,5-triazine-2,4-diamine |
| tetrafluron | N,N-dimethyl-N'-[3-(1,1,2,2-tetrafluoroethoxy)phenyl]urea |
| thiazafluron | N,N'-dimethyl-N-[5-(trifluoromethyl)-1,3,4-thiadiazol-2-yl]urea |
| thiazopyr | methyl-2-(difluoromethyl)-5-(4,5-dihydro-2-thiazolyl)-4-(2-methylpropyl)-6-(trifluoromethyl)-3-pyridinecarboxylate |
| thifensulfuron | 3-[[[[(4-methoxy-6-methyl-1,3,5-triazin-2-yl)amino]carbonyl]amino]sulfonyl]-2-thiophenecarboxylic acid |
| thiobencarb | S-[(4-chlorophenyl)methyl]diethylcarbamothioate |
| 2,2,3-TPA | 2,2,3-trichloropropionic acid |
| triallate | S-(2,3,3-trichloro-2-propenyl) bis(1-methylethyl)carbamothioate |
| triasulfuron | 2-(2-chloroethoxy)-N-[[(4-methoxy-6-methyl-1,3,5-triazin-2-yl)amino]carbonyl] benzenesulfonamide |
| tribenuron | 2-[[[[(4-methoxy-6-methyl-1,3,5-triazin-2-yl)methylamino]carbonyl]amino]sulfonyl]benzoic acid |
| tricamba | 2,3,5-trichloro-6-methoxy benzoic acid |
| triclopyr | [(3,5,6-trichloro-2-pyridinyl)oxy]acetic acid |
| tridiphane | 2-(3,5-dichlorolphenyl)-2-(2,2,2-trichloroethyl)oxirane |
| trietazine | 6-chloro-N,N,N'-triethyl-1,3,5-triazine-2,4-diamine |
| trifluralin | 2,6-dinitro-N,N-dipropyl-4-(trifluoromethyl)benzenamine |
| triflusulfuron | 2-[[[[4-(dimethylamino)-6-(2,2,2-trifluoroethoxy)-1,3,5-triazin-2-yl]amino]carbonyl]amino]sulfonyl]-3-methylbenzoic acid |
| trimeturon | methyl N'-(4-chlorophenyl)-N,N-dimethylcarbamidate |
| tritac | 1-[(2,3,6-trichlorophenyl)methoxy]-2-propanol |
| vemolate | S-propyl dipropylcarbamothioate |
| xylachlor | 2-chloro-N-(2,3-dimethylphenyl)-N-(1-methylethyl)acetamide |

*source http://piked2.agn.uiuc.edu/wssa/subpages/herbicide/herbtab.htm

Also within the scope of the present invention is the stimulation of the activity of an ecto-phosphatase and an ABC transporter by the over-expression of a regulatory molecule which may act by up-regulating the expression levels or by post-translationally modifying the ecto-phosphatase and the ABC transporter. Such activating regulatory molecules (e.g. calmodulin) may be over-expressed alone or together with the over-expression of the ecto-apyrase and the ABC transporter or any other combination.

Particular embodiments of the invention include polynucleotides that encode MDR-ABC transporter polypeptides, ecto-phosphatase polypeptides, and stimulatory regulatory polypeptides which are capable of stimulating the efflux of drug molecules from the cells, thus conferring drug resistance. The term polynucleotide encompasses nucleic acid molecules that encode a complete protein, as well as nucleic acid molecules that encode peptides, polypeptides, or fragments of a complete protein. The polynucleotides may comprise the wild-type allele (or a portion of such an allele) of a functional peptide ABC transporter and ecto-phosphatase, or they may comprise a mutated allele of such genes. The preferred polynucleotides encode the wild-type plant, *Arabidopsis thaliana,* AtPGP-1 ABC transporter (GenBank accession # X61370); wild-type *Homo sapiens* Pgp ABC transporter (GenBank accession # M29432); wild-type *Homo sapiens* MRP-β ABC transporter (PCT WO 98/46736); wild-type yeast, *Saccharomyces cerevisiae,* transporter STS1 (GenBank accession # X75916); wild-type yeast, *Saccharomyces cerevisiae,* transporter Pdr5p (GenBank accession # 1420383); wild-type *Aspergillus fumigatus* Afu-MDR1 ABC transporter (U.S. Pat. No. 5,705,352); wild-type bacterial, *Lactococcus lactis,* transporter LmrA (GenBank accession # U63741); wild-type plant, *Pisum sativum,* ecto-phosphatase, apyrase (GenBank accession # Z32743); and for wild-type *Homo sapiens* apyrase (GenBank accession # AF034840); other ecto-phsophatases include *Homo sapiens* CD39L2 (GenBank accession # AF039916); *Homo sapiens* CD39L3 (GenBank accession # AF039917); *Homo sapiens* CD39L4 (GenBank accession # AF039918); and *Homo sapiens* ATP diphosphohydrolase (GenBank accession # HSU87967).

In one embodiment of the invention, the polynucleotides are operably linked to regulatory sequences sufficient to permit the expression of the polynucleotide in a host cell. Such polynucleotides may be incorporated into nucleic acid vectors that are sufficient to permit either the propagation or maintenance of the polynucleotide within a host cell, and expression therein. The nature of the regulatory elements will depend upon the host cell, and the desired manner of expressing the polynucleotides.

The invention particularly contemplates providing the polynucleotides to plants. Suitable plants include, but are not limited to, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Bromelia, Glycine, Lolium, Zea, Triticum, Sorghum, Ipomoea, Passiflora, Cyclamen, Malus, Prunus, Rosa, Rubus, Populus, Santalum, Allium, Lilium, Narcissus, Ananas, Arachis, Phaseolus, Pisum, Oryza, Hordeum, Gossypium.

Preferred prokaryotic vectors for subcloning and production of DNA include plasmids such as those capable of replication in *E. coli* such as, for example, pBR322, ColE1, psC101, pACYC184, such as those disclosed by Maniatis, T., et al. (In: *Molecular Cloning, A Laboratory Manual,* Cold Spring Harbor Press, Cold Spring Harbor, N.Y. (1982)); pET11a, pET3a, pET11d, pET3d, pET22d, pET12a, pET28a, and other pET variants (Novagen); pCDNA3, pCDNA1 (InVitrogen).

A variety of methods may be used to introduce the polynucleotides of the present invention into a plant cell. Some examples include, but are not limited to, microinjection directly into the plant embryo cells or introduced by electroporation as described in Fromm et al., 1985, *Proc. Natl. Acad. Sci. USA* 82:5824–5828; direct precipitation using polyethylene glycol as described in Paszkowski et al., 1984, *EMBO J.* 3:2717–2722; in the case of monocotyledonous plants, transformation of pollen with total DNA or an appropriate functional clone and the pollen can then be used to produce progeny by sexual reproduction; introduction of polynucleotides with the Ti plasmid of *Agrobacterium tumefaciens* which provides a means for introducing DNA into plant cells (Horsch et al., 1988, *Current Communications in Molecular Biology,* Cold Spring Harbor Press, Cold Spring Harbor, N.Y., pp 13–19); introduction of polynucleotides with the cauliflower mosaic virus (CaMV) (U.S. Pat. No. 4,407,956).

A particularly useful Ti plasmid-based vector is Pkylx71. Schardl, C. et al., 1987, *Gene* 61:1–11. This vector utilizes the natural transfer properties of the Ti plasmid. A cloning vehicle such as pKYLX71 allows the insertion of a polynucleotide sequence into the expression cassette by a single recombination event.

The introduction of the transferred DNA (T-DNA) of the plasmid is accomplished by infecting root calli from Ws ecotype *Arabidopsis thaliana* with *Agrobacterium tumefaciens* under kanamycin selection. The calli are then developed further into plants. Valvekens, D., 1992, *Proc. Natl. Acad. Sci. USA* 85:5536–5540. Alternatively, shoot explants may be infected with the *Agrobacterium tumefaciens* bacteria. Under appropriate conditions, a ring of calli forms around the cut surface which is then transferred to growth medium, allowed to form shoots, roots and develop further into plants. Hooykass, P. J. J. et al., In: *Molecular Form and Function of the Plant Genome,* Plenum Press, N.Y. pp 655–667 (1984). Another alternative is to produce transformed plants using free DNA delivery. All plants from which protoplasts can be isolated and cultured to give whole regenerated plants can be transformed by the present invention so that whole plants are recovered which contain the introduced polynucleotide. Methods for generating plants from cultured protoplasts are described by Binding, H. In: *Plant Protoplasts,* CRC Press, Boca Raton, pp. 21–37 (1985), incorporated herein by reference.

Efficient plant promoters that may be used to over-express the ABC transporters and the ecto-phosphatases include over-producing plant promoters such as the small subunit (ss) of the ribulose 1, 5 biphosphate carboxylase from soybean (Berry-Lowe et al., 1982, *J Molec. App. Gen.* 1:483–498), the promoter of the chlorophyll a/b binding protein, and the CaMV promoter.

Parts obtained from the recombinant plant such as flowers, seeds, leaves, branches, bark, fruit, etc, are covered by the invention. Progeny, variants, and mutants of the recombinant plants are also included within the scope of this invention.

Conference of Drug Resistance in Microorganisms

The present invention is also directed to a method for the conference of drug resistance to microorganisms, including yeast and bacteria in part through the manipulation of the ATP gradient across biological membranes. In yeast and bacteria, the manipulation of extracellular ATP levels and the ATP gradient across biological membranes by the over-expression of a MDR-ABC transporter and/or an ecto-phosphatase may result in resistance to certain drugs. Such resistance is useful for the growth of microorganisms for biotechnological applications, e.g., those used in heterologous protein production.

It is particularly advantageous to be able to produce microorganisms which are resistant to a variety of drugs for large scale fermentation procedures where contamination by microorganisms from the environment may threaten a costly procedure. Additionally, the present invention is useful to create resistant microorganism strains in small scale fermentation processes, industrial applications, as well as in selection systems for the production of recombinant microorganisms for research applications. Research applications may include the use of resistant microorganism strains to study alternative pathways, other than antibiotics, antifungal reagents, or other commonly used drugs which could effectively inhibit the growth of microorganisms involved in disease states of humans and animals.

In yeast, a system which could confer drug resistance may be preferred to current research techniques which utilize yeast strains deficient for certain amino acid production pathways. These deficient yeast are used to introduce foreign nucleic acids of interest having a nucleotide sequence encoding a protein or proteins capable of resurrecting a deficient amino acid production pathway. Selection occurs when the yeast is grown in media deficient in that particular amino acid. This method of conferring resistance to yeast may be costly, however, since this requires that the yeast be grown in expensive cocktails of the amino acids in which they are deficient. In certain embodiments of the present invention, a cloning system in yeast confers drug resistance to the yeast coupled to the introduction of a nucleic acid molecule of interest. Such resistance may be constitutive or inducible. The yeast may then be selected by the introduction of inexpensive drugs to which the recombinant yeast would be resistant.

In other embodiments of the invention, bacteria may be produced with increased resistance to certain drugs in order to facilitate the production and to provide a system which allows for selection of bacteria based on another mechanism other than antibiotic resistance. Such resistance may be constitutive or inducible and may be particularly useful in large scale fermentation where contamination by other microorganisms is more likely to occur.

Also contemplated by the present invention is the development of microorganisms which grow in soil (soil flora), particularly those designed to interact with herbicide resistant plants. The soil flora may be engineered with the same resistance to toxins as the plants with which they are engineered to react.

Additionally, the invention is directed to the development of microorganisms which are resistant to multiple toxins (two-stage resistant microorganisms or multiple-stage resistant microorganisms). The toxins could be presented to such two-stage resistant organisms or multiple-stage microorganisms simultaneously or at independent times. The present invention also contemplates the development of two-stage or multiple-stage resistant plants.

In one embodiment of the invention, the over-expression of an ecto-phosphatase confers drug resistance in wild-type or genetically engineered microorganisms. This effect was seen in yeast cells over-expressing plant apyrase grown in the presence of cycloheximide, a potent inhibitor of protein expression.

In another embodiment of the invention, the over-expression of an ABC transporter confers drug resistance in wild-type and genetically engineered microorganisms. In a preferred embodiment, the ABC transporter which is over-expressed is the Arabidopsis thaliana ABC transporter AtPGP-1. This ABC transporter was able to confer resistance to yeast cells grown in the presence of cycloheximide.

In a further embodiment of the invention the affect of over-expression of both an MDR-ABC transporter and an ecto-phosphatase is to enhance the ATP gradient across biological membranes and thus stimulate the resistance to certain antimicrobial agents. In a particularly preferred embodiment of the invention the MDR-ABC transporter which is over-expressed is the Arabidopsis thaliana AtPGP-1 and the ecto-phosphatase that is over-expressed is Pisum sativum apyrase.

The invention particularly contemplates, but is not limited to, the conference of resistance in microorganisms to cycloheximide, antibiotics, antifungal agents, pheromones, heavy metals, flourescent dyes, DNA intercalating agents, products of plant secondary metabolism such as polyphenolics and alkaloids, plant growth substances with antimicrobial properties, and the chemicals listed in Table 1 above.

In one embodiment of the invention, the nucleic acids are operably linked to regulatory sequences sufficient to permit the transcription of the nucleic acid in the microorganism of interest. Such constructs may be incorporated into nucleic acid vectors that are sufficient to permit either the propagation or maintenance of the nucleic acid and expression thereof within the host cell. The nature of the regulatory elements is dependent upon the host cell, and the desired manner of expressing the nucleic acid (e.g. constitutively or inducibly).

The invention particularly contemplates providing the nucleic acids of interest to bacteria and yeast. Suitable bacteria include both archaebacteria, which are found in incommodious environments such as bogs, ocean depths, salt brines, and hot acid springs (e.g. sulfur bacteria, extreme halophiles, methanogens), and eubacteria, which are the commonly encountered forms that inhabit soil, water, and larger living organisms (e.g. gram positive, anaerobic, blue-green algae, gram negative, and spirochetes). In a preferred embodiment, the bacteria are Escherichia coli. Suitable yeast include a large group of disparate organisms. Preferred species include the budding yeast, Saccharomyces cerevisiae, and the fission yeast, Schizosaccharomyces pombe.

Preferred prokaryotic vectors include, but are not limited to, plasmids such as those capable of replication in E. coli, for example, pBR322, ColE1, psC101, pACYC 184 such as those disclosed by Maniatis, T., et al. (In: Molecular Cloning, A Laboratory Manual, Cold Spring Harbor Press, Cold Spring Harbor, N.Y. (1982)); pET11a, pET3a, pET11d, pET3d, pET22d, pET12a, pET28a, and other pET variants (Novagen); pCDNA3, pCDNA1 (InVitrogen); pRR54, pRS303, pEGFP-1, pBluescript SK, pTrc99A,B,C and their derivatives (In: Current Protocols in Molecular Biology, John Wiley & Sons, Inc., Mass., USA (1998)); pGEX variants (Pharmacia) and bacteriophages (e.g. Lambda phages).

Preferred yeast vectors include plasmids such as those capable of replication in either Saccharomyces cerevisiae or Schizosaccharomyces pombe. These vectors include, but are not limited to, pYES2, pVT101, Yip5, Prp7, Yrp17, Pep13, Yep24, Ycp19, Ycp50, Ylp21, pYAC3, 2 μm, pLG670. In: Current Protocols in Molecular Biology, John Wiley & Sons, Inc., Mass., USA (1998).

A variety of methods may be used to introduce the polynucleotide sequences into a microorganism. In bacteria for example, techniques such as transformation of plasmid DNA using calcium chloride competent cells, high efficiency competent cells, electroporation, or infection by bacteriophages as described in *Current Protocols in Molecular Biology,* John Wiley & Sons, Inc., Mass., USA (1998) may be used.

In yeast, methods to introduce polynucleotides can include, but are not limited to, the introduction of polynucleotides by integrative transformation, transformation by electroporation, spheroplast transformation, transformation using lithium acetate as described in *Current Protocols in Molecular Biology,* John Wiley & Sons, Inc., Mass., USA (1998) and PEG lithium acetate transformation procedure (Eble, R., 1992, *Biotechniques* 13:18–20).

Also within the scope of the present invention is the conference of drug resistance to eukaryotic cell lines grown in tissue culture, including insect cell lines and mammalian cell lines. The conference of drug resistance to eukaryotic cell lines may be useful in the use of such cell lines for the production of recombinant proteins, the study of chemotherapeutic resistance in cells from various sources, and in the study of toxic levels of drugs in certain resistant cell lines.

Preferred eukaryotic vectors include but are not limited to, viral vectors, naked nucleic acids, plasmids, shuttle vectors, complexes of nucleic acids and other molecules, such as polycations (e.g. cationic lipids), including those described in *Current Protocols in Molecular Biology,* John Wiley & Sons, Inc., Mass., USA (1998) for introduction of heterologous DNA in mammalian cells and those described in Baculovirus Expression Vectors; a laboratory manual, Oxford University Press, New York., N.Y. (1994) for introduction of heterologous DNA in insect cells.

Inhibition of Drug Resistance in Chemotherapy

In an alternative embodiment of the invention, modulation of the ATP gradient, specifically the suppression of the gradient, may be achieved by inhibiting the activity of the ecto-phosphatase and the ABC transporter. Suitable inhibitor mechanisms include, but are not limited to, the use of small molecules which may bind to and inhibit the activity of the ecto-phosphatase and small molecules which may bind to and inhibit the ABC transporter. Other suitable inhibitor mechanisms include, but are not limited to, the expression of anti-sense RNA molecules which may inhibit the transcription or translation of ecto-phosphatases and ABC transporters, as well as the expression of dominant negative mutants of the ecto-phosphatase and the ABC transporters which may act to interfere with and inhibit the activity of their wild-type counterparts. Also within the scope of the invention is the over-expression of regulatory molecules which inhibit the activity of the ecto-phosphatase and the ABC transporter. The ecto-phosphatase may be inhibited alone or together with the ABC transporter.

The present invention provides for methods for the transcription of exogenous antisense RNA, in vivo or in vitro, comprising the administration of a polycistronic vector which may contain nucleic acid molecules from which may be transcribed an antisense RNA complementary to an ecto-phosphatase RNA molecule and an ABC transporter RNA molecule. The ecto-phosphatase nucleic acids and the ABC transporter nucleic acids may be operatively linked to a constitutive promoter or an inducible promoter (e.g. the constitutive major intermediate early promoter of cytomegalovirus or the inducible metallothionine promoter). Also within the scope of the invention are multiple vectors whereby the ecto-phosphatase nucleic acid and the ABC transporter nucleic acid are incorporated into separate vectors.

The present invention also provides for methods for the expression of exogenous regulatory molecules or small molecules, in vivo or in vitro, comprising the administration of a polycistronic vector or multiple vectors which may incorporate nucleic acid molecules encoding for regulatory proteins, or small molecules capable of inhibiting the activity of an ecto-phosphatase and an ABC transporter. These nucleic acids which encode for regulatory molecules may be operatively linked to either a constitutive promoter or an inducible promoter as described above.

In certain preferred embodiments, only the endogenous ecto-phosphatase is inhibited by antisense RNA, regulatory proteins, or small molecules. In other embodiments of the present invention, both the endogenous ecto-phosphatase and the ABC transporter are targeted for inhibition.

In particularly preferred embodiments, the ecto-phosphatase is human apyrase (e.g. GenBank accession # AF034840, AF039916, AF039917, AF039918, HSU87967) and the MDR-ABC transporter is human MDR-1, (e.g. human P-glycoprotein MDR-1, GenBank accession # M29432 and human MRP-β PCT, publication WO 98/46736).

The nucleic acid molecules from which will be transcribed antisense RNA molecules described above or the nucleic acid molecules encoding for regulatory molecules as described above may be incorporated into any suitable cloning or expression vector, operably linked to appropriate control elements (e.g. promoter elements, enhancer elements, ribosomal binding sites, polyadenylation sites, termination sites, etc.). Examples of such vectors include, but are not limited to, herpes simplex viral based vectors such as pHSV1 (Geller et al., 1990, *Proc. Natl. Acad. Sci. U.S.A.* 87:8950–8954); retroviral vectors such as MFG (Jaffee et al., 1993, *Cancer Res.* 53:2221–2226), and in particular Moloney retroviral vectors such as LN, LNSX, LNCX, LXSN (Miller and Rosman, 1989, *Biotechniques* 7:980–989); vaccinia viral vectors such as MVA (Sutter and Moss, 1992, *Proc. Natl. Acad. Sci. U.S.A.* 89:10847–10851); adenovirus vectors such as pJM17 (Ali et al., 1994, *Gene Therapy* 1:367–384; Berker, 1988, *Biotechniques* 6:616–624; Wand and Finer, 1996, *Nature Medicine* 2:714–716); adeno-associated virus vectors such as AAV/ neo (Mura-Cacho et al., 1992, *J. Immunother.* 11:231–237); lentivirus vectors (Zufferey et al., 1997, *Nature Biotechnology* 15:871–875). Such vectors may be targeted to the tumor cells of interest as described in U.S. Pat. Nos. 5,834,256, 5,843,742, 5,830,727, 5,814,500.

Administration of the foregoing agents may be local or systemic, using a suitable physiological carrier. Other compounds which aid in the uptake or stability of these agents, or which have beneficial activity, may also be included in the formulations of the invention.

Inhibition of Drug Resistance in Microorganisms to Treat Infection

The present invention also relates to methods for inhibiting or ameliorating infection in animals and humans caused by microorganisms, particularly bacterial and fungal infections using inhibitory mechanisms against an ecto-phosphatase and an ABC transporter and modifying the ATP gradient across biological membranes. The invention is useful in the inhibition or amelioration of a wide range of infections including, but not limited to, gram-negative bacterial infection including gram-negative sepsis, gram-negative endotoxin-related hypotension and shock, rabies, cholera, tetanus, lymes disease, tuberculosis, *Candida albicans,* Chlamydia, etc. The invention is based, in part, on the unexpected result that when mutant yeast deficient in two potent extracellular ATP phosphatases were cultured in cycloheximide, they were not able to grow. Surprisingly, they were rescued by the over-expression of a plant MDR-ABC transporter AtPGP-1, suggesting that the inability to grow in the drug was caused by an inability to efflux the drug which was coupled to a deficiency in extracellular ATP phosphatase activity.

Drug sensitivity in microorganisms may be achieved by introducing nucleic acid molecules into bacteria and yeast (as described above) that are capable of conferring inhibition of the activity of an endogenous ecto-phosphatase and an ABC transporter. Such nucleic acid molecules may transcribe an antisense RNA complimentary to endogenous RNA for an ecto-phosphatase or an ABC transporter, encode for inhibitory regulatory proteins, or encode for inhibitory drug molecules. The inhibition or amelioration of the infections may involve the administration of an anti-microbial agent (such as an antibiotic or an antifungal agent) with the concurrent administration of the aforementioned nucleic acid molecules (which may be achieved through bacteriophages, etc).

Additionally, the present invention is useful in the development of genetic and epigenetic systems in humans for resistance to toxins from biological and non-biological sources. Such sources include, but are not restricted to, pathogens produced by microbial infections, pathogens and toxins derived from biological sources through human contrivance, environmental toxins not produced through biological action, and toxic substances created synthetically. In a particular embodiment, humans at risk for exposure would be vaccinated either with a gene therapy designed to bolster endogenous ATP gradients in human cells, or a chemical substance capable of enhancing the strength of the ATP gradient. In both instances, the target of the genetic or chemical therapy would be either the ABC transporter activity, ecto-phosphatase activity or both. In another embodiment of the invention, only the ABC transporter activity or the ecto-phosphatase activity in an infecting organism is diminished to inhibit drug efflux. Recombinant techniques may be used to introduce DNA sequences to the microorganism which encode for a small inhibitory molecule to either an ABC transporter or an ecto-phosphatase or both to cause the inhibition of drug efflux from the microorganism.

The present invention is further illustrated by the following examples which in no way should be construed as being further limiting. The contents of all references cited throughout this application are hereby expressly incorporated by reference.

EXAMPLE 1
Over-Expression of Ecto-Phosphatase does not Increase the Cellular Uptake of Adenosine
Materials and Methods Transgenic Plant Construction: psNTP9 (*Pisum Sativum* apyrase, GenBank accession #Z32743) was subcloned as a SalI to XbaI fragment into pKYLX71 (Schardl et al, 1987, supra.). This plasmid was transformed into *A. tumefaciens* GV3101 [pMP90] pKYLX71 (Koncz, C. and Shell, J., 1986, *Mol. Gen. Genet.* 204:383–396.), which was used to infect root calli from Ws ecotype *Arabidopsis thaliana* under kanamycin selection (Valvekens, D. et al., 1992, *Proc. Natl. Acad. Sci. USA* 85:5536–5540.). Four individual lines, obtained from separate calli, were propagated to the third generation (T3).

Subcellular Apyrase Distribution in Pea: Etiolated pea plumules served as the tissue source for nuclei and cytoplasm isolation as described by Chen and Roux (*Plant Physiol.* 81:609–612 (1986)). Plasma membrane was prepared from 30 g of pea root tissue (Zhu Mei Jun and Chen Jia, 1995, *Acta Botanica Sinica* 37:942–949). Western analysis was performed on 15–30 $\mu$g of protein from cytoplasm, plasma membrane and nuclei using a polyclonal anti-apyrase antibody raised against the purified pea protein (Tong, C. et al., 1993, *Plant Physiol.* 101:1005–1011). To determine the orientation of the pea apyrase in the pea plasma membrane, outside-out vesicles were prepared (Short et al., supra.), and the accessibility of the enzyme was determined by selective trypsin proteolysis, or membrane shaving, followed by activity assays and western blotting.

Phosphate uptake experiments and growth assays: In all experiments the growth media did not contain sugar, and plants were grown in sterile culture at 22° C. under 150–200 $\mu$E of continuous light. Unless otherwise noted, a standard 0.8% agar medium (Becton Dickenson, Cockeysville, Md.) containing 100 $\mu$M phosphate was used for uptake assays (Somerville, C. et al., 1982, *Methods in Chloroplast Biology,* Elsevier Biomedical Press, Amsterdam, pp 129–138). Plants used for the phosphate uptake experiments were grown singly in 1 ml of the standard agar medium for 15 days prior to the experiment. On the day of the experiment, 10 $\mu$Ci $^{32}$P was applied to the side of the culture dish and allowed to diffuse through the agar. The lids of 95 mm×15 mm tissue culture dishes (Fisher, Pittsburgh, Pa.) were removed to facilitate transpiration. After 18 hours, the plants were removed from the medium. The aerial portions of the plant not in contact with the agar were weighed and counted by liquid scintillation. For each plant the entire root system was carefully pulled from the agar and washed in ice cold water prior to scintillation counting. To measure the transport of the products of ATP hydrolysis by the transgenic plants overexpressing apyrase and by wild-type plants, [2,8$^3$H] ATP, [$\alpha^{32}$P]ATP, and [$\gamma^{32}$P]ATP (Amersham) were fed to 15-day-old plants in separate treatments. All treatments were analyzed for significance in a T-test (n>4–6 for all groups, *P<0.05, error bars=s.e.m.).

Results

Detection of the pea apyrase in nuclei and in purified plasma membrane: By immunoblot assay, the pea apyrase was found to be associated with nuclei and with purified plasma membranes but not with the cytoplasm (FIG. 1A). The contents of the lanes in FIG. 1A are as follows: Lane 1, cytoplasm; Lane 2, purified plasma membrane; Lane 3, purified nuclei; and Lane 4, pre-immune control of nuclei. Protease treatment destroyed both apyrase activity and antigenicity in outside-out plasma membrane vesicles. After trypsin treatment, the exterior face of the vesicle showed 30% of the ecto-phosphatase activity of the untreated sample. Endo-phosphatase activities were retained after trypsin treatment, indicating that the digest occurred exclusively on the exterior face of the membrane. These data indicated that the ecto-apyrase was in fact being expressed in the extracellular matrix (ECM).

Figure 1B:
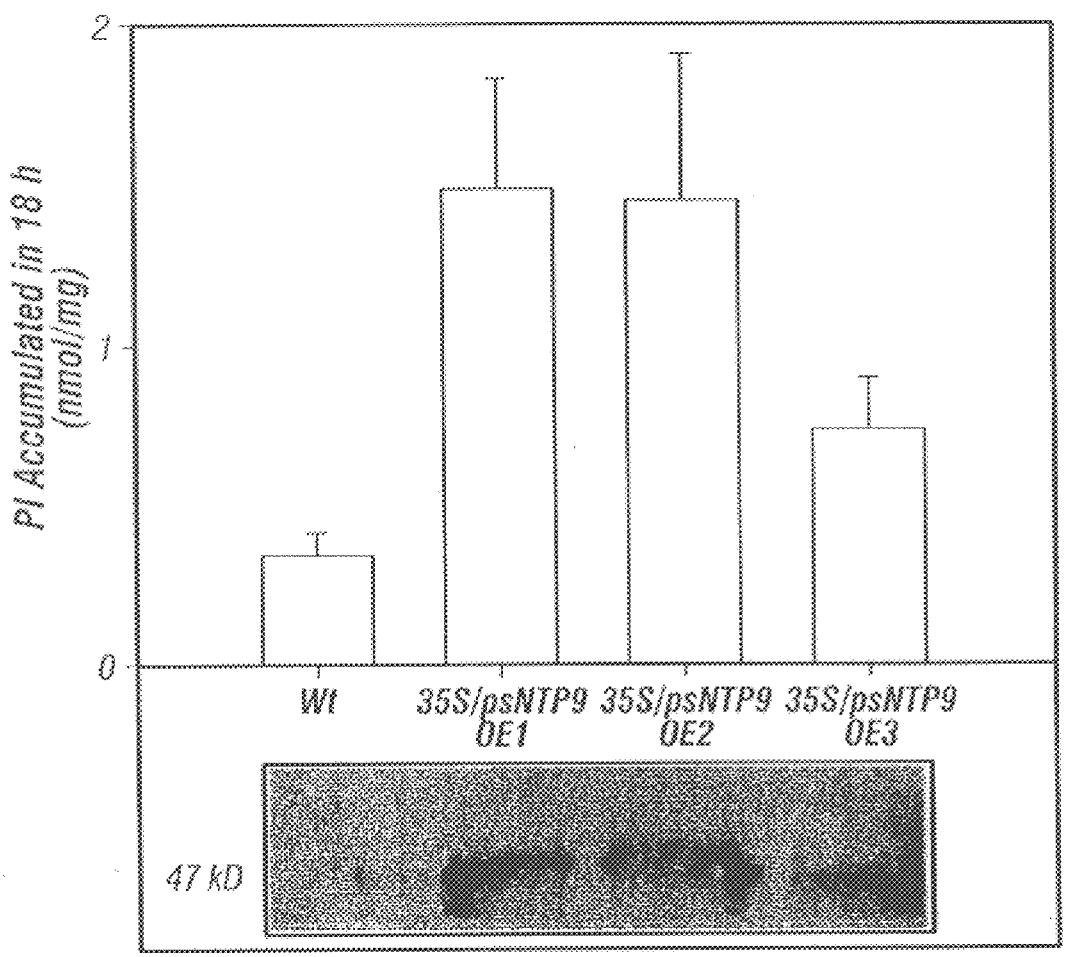
Figure 1C:
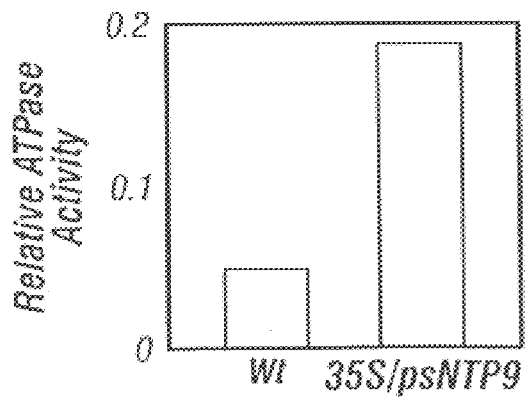

Enhanced Growth of Plants Over-Expressing Apyrase: Three of the four transgenic plant lines constitutively expressed psNTP9 under the control of the cauliflower mosaic virus 35S promoter and over an 18 hour period showed two to five times as much phosphate accumulation in shoots as wild type (FIG. 1B); Top, the total phosphate accumulated in the shoots of three independent transformants in an 18 hour $^{32}$P uptake assay at 2 mM phosphate; Bottom, a corresponding immunoblot performed on equal amounts of protein isolated from the ECM of three week-old wild-type *Arabidopsis thaliana* and the psNTP9 transgenics. Apyrase expressing plants also showed four times as much phosphatase activity in the extracellular matrix as the wild-type (FIG. 1C). (Note, OE1 in the figure stands for over-expression 1 transgenic line).

Figure 2A:
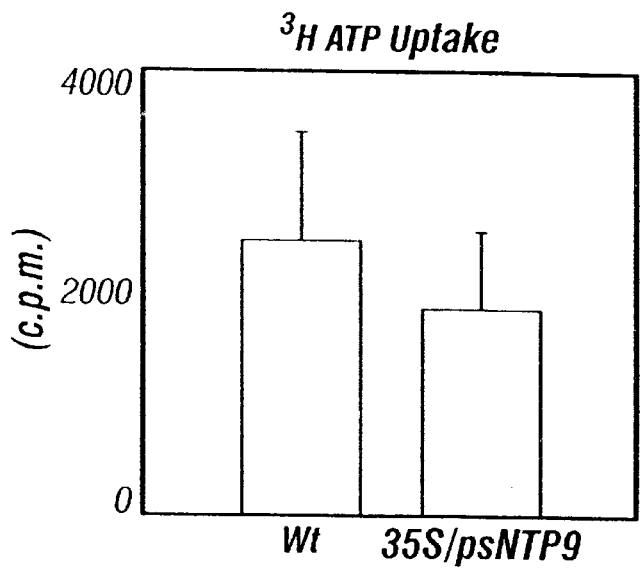
FIGS. 2A, 2B, 2C. Transport of the products of ATP hydrolysis by transgenic plants overexpressing apyrase and by wild-type plants.
Figure 2B:
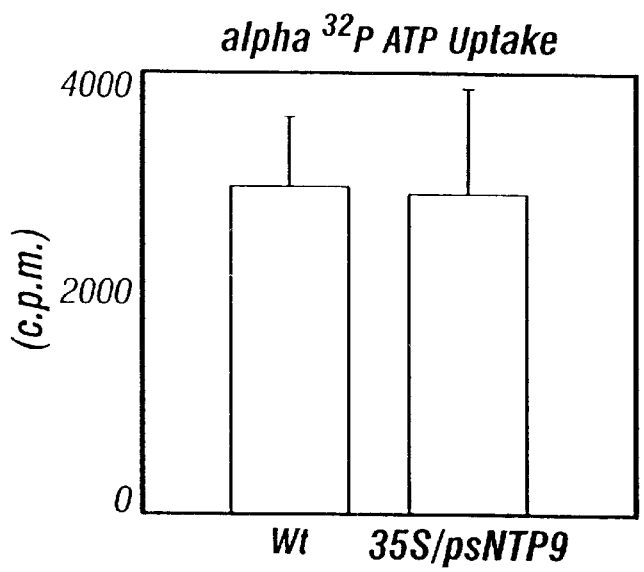
Figure 2C:
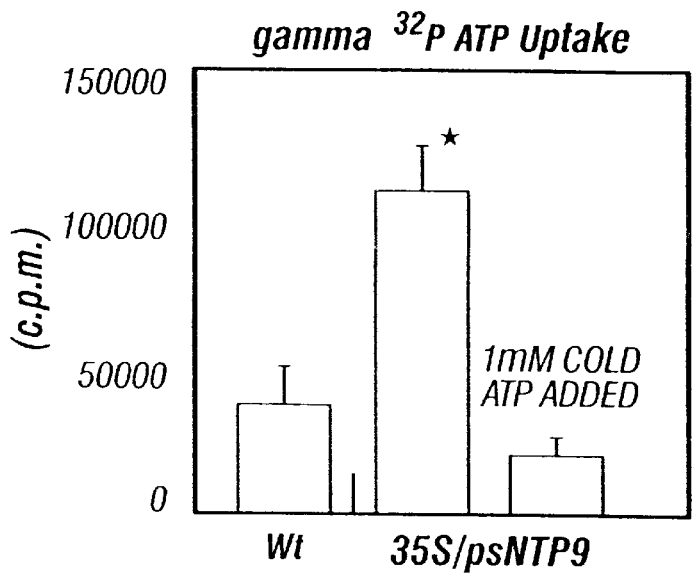
Figure 4A:
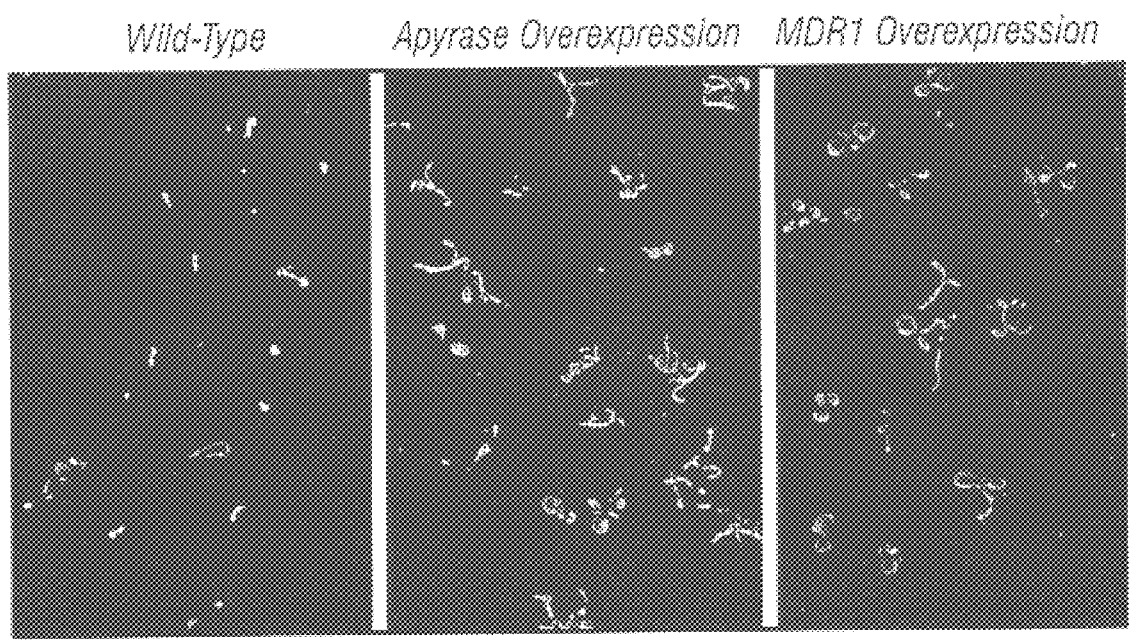
FIG. 4A, 4B-1, 4B-2, 4B-3. Conference of resistance to cycloheximide (A) and cytokinin (B-1, B-2, B-3) in Arabidopsis plants over-expressing either the ecto-phosphatase, apyrase, or the ABC transporter, AtPGP-1.
Figures 1, 4B:
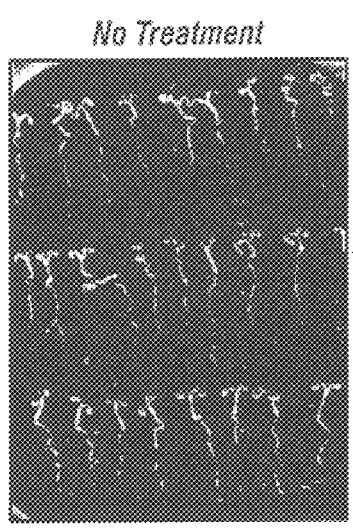
Figures 2, 4B:
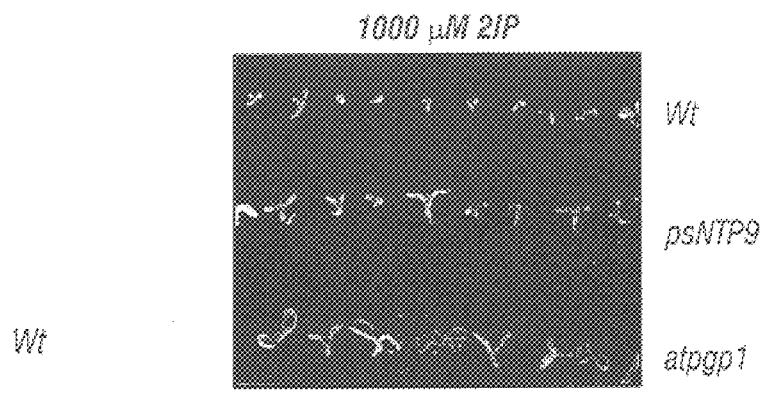

Transgenic plants preferentially transport the gamma phosphate of ATP: In order to address whether over-expression of ecto-apyrase was stimulating the adenosine salvage pathway, the intracellular uptake of adenosine was measured both in the presence and absence of the over-expression of apyrase. The inability of apyrase to translocate either extracellular AMP or adenosine was demonstrated by the low level of radiolabel accumulated in the transgenic plants fed [2,8$^3$H]ATP and [$\alpha^{32}$P]ATP (FIG. 2). The complete dephosphorylation of [2,8$^3$H]ATP would result in a radiolabelled adenosine molecule while the complete dephosphorylation of [$\alpha^{32}$P]ATP would result in a non-labeled adenosine label. FIG. 2A illustrates that plants overexpressing apyrase did not translocate radiolabelled adenosine (or byproducts of the dephosphorylation of [2,8$^3$H]ATP) any more efficiently than plants not overexpressing apyrase (wild-type plants). FIG. 2B illustrates that plants overexpressing apyrase did not translocate AMP (or the byproducts of the dephosphorylated [$\alpha^{32}$P]ATP) any more efficiently than wild-type plants. In comparison, feeding experiments where the γ phosphate was labeled, the transgenics accumulated three times the amount of labeled phosphate as the wild-type (FIG. 2C). These data show that the over-expression of apyrase does not induce an increase in the uptake of adenosine and therefore its over-expression does not act to stimulate the adenosine salvage pathway.

EXAMPLE 2
Ecto-Phosphatase is Involved in Drug Resistance in Yeast and Plants
Materials and Methods Expression of AtPGP-1 in yeast: The AtPGP-1 cDNA (*Arabidopsis thaliana* MDR gene, accession #X61370) was subcloned into pVT101 downstream of the ADH promoter to create the AtPGP-1/pVT101 construct. AtPGP-1/pVT101 and pVT101 were transformed into *Saccharomyces cerevisiae* INVSC1 (genotype: MATα, his3-Δ1, leu2, trp1-289, ura3-52) and YMR4 (genotype: MATαhis3-11,15, leu2-3, 112ura3Δ5, can Res pho5, 3::ura3Δ1) by a PEG lithium acetate procedure (Eble, R., 1992, *Biotechniques* 13:18–20) and selected on uracil dropout medium.

Yeast Growth: Yeast were grown at 30° C. under conditions of constant selection for uracil auxotrophy. YNB (Bio101, Vista, Calif.) supplemented with CSM (uracil dropout) and 2% glucose was used to grow strains having pVT101 constructs. Cycloheximide (Sigma Chemical, St. Louis, Mo.) was added to liquid media or spread on solid media to achieve a final concentration of 500 ng/ml. Nigericin (Sigma Chemical, St. Louis, Mo.) was added to liquid media or spread on solid media to achieve a final concentration of 25 μg/ml. Yeast strains used in cycloheximide selection assays were always propagated in the presence of the cycloheximide on plates and then streaked onto new plates containing drug or no drug, such that induced resistance existed in each strain at the time of the start of the assay. For selection assays on plates, single colonies were streaked; for selection in liquid media 0.01 ml of saturated culture was added to fresh media containing the drug. The plates shown in figures were grown for 3–5 days before photographs were taken. Yeast selection assays in liquid media were quantitated by turbidity as measured by absorbance at $OD_{600}$.

Expression of apyrase and AtPGP-1 in plants: The expression of apyrase in plants is as described above in Example 1. Similar methods were employed to express AtPGP-1 in *Arabidopsis thaliana* plants with the following modifications. The AtPGP-1 coding region was subcloned into a pBIN vector lacking the GUS gene as described in Sidler, et al., 1998, *The Plant Cell* 10:1623–1636. This plasmid was then transformed into *A. tumefaciens* as described above, which was used to infect root calli to produce transgenic plants expressing AtPGP-1.

Plant growth: *Arabidopsis thaliana* seeds were sown in a solid germination media containing MS salt, 2% sucrose, 0.8% agar, and vitamins (Valvekens, D. et al., 1992, *Proc. Natl. Acad. Sci. USA* 85:5536–5540. For selection assays, cycloheximide was spread on the media to achieve a final concentration of 250 ng/ml. Plant growth was measured by germination percentage after 6–30 days.

Results

Figures 3, 4B:
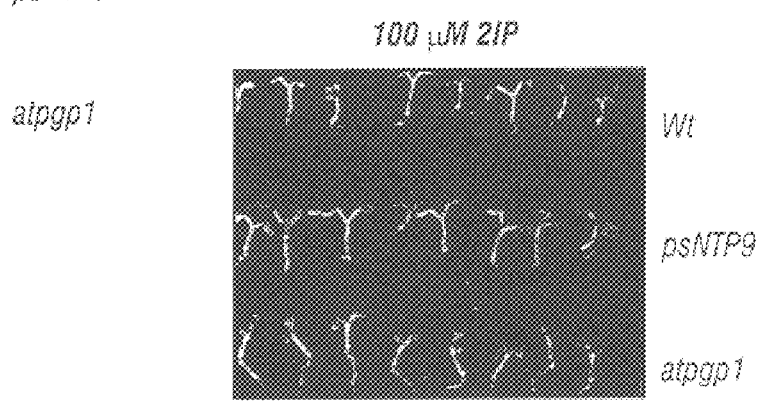

Effect of over-expression of AtPGP-1 in veast: When a yeast mutant, YMR4, which is deficient in two major extracellular phosphatases and tends to accumulate ATP extracelluarly, was grown in a potent cellular toxin, cycloheximide, it did not grow whereas a wild-type yeast strain, INVSC1, did grow in the presence of cycloheximide (FIG. 3A). Surprisingly, expression of the plant multidrug resistance (MDR) gene, AtPGP-1, enabled the yeast mutant to grow in the toxin (FIG. 3B and FIG. 5A). The presence of AtPGP-1 in the wild-type yeast did not have any effect when grown in the presence of cycloheximide (FIG. 3B). The same result was obtained when the yeast strains were cultured in nigericin (FIGS. 3C, 3D, FIGS. 5B, 5C). In FIG. 3C and 3D, starting from the top of the dish clockwise, the cells are as follows: INVSC1 (wild-type) overexpressing AtPGP-1, YMR4 containing the vector alone, YMR4 over-expressing AtPGP-1, and INVSC1 containing the vector alone. When grown without drug, all the cells grow (FIG. 3C). However, when grown in drug, only the YMR4 containing vector alone shows reduced growth. The survival of the AtPGP-1 transformed strains was due to the ability of the MDR1 channel to efflux the toxin, hence lowering the actual cellular concentration of the poison cycloheximide. The sensitivity of the untransforned mutant to the drug is likely due to a loss of the ATP gradient below a point at which endogenous transporters, similar to AtPGP-1 can function.

Effect of over-expression of AtPGP-1 in plants: The over-expression of AtPGP-1 was able to confer resistance to cycloheximide in plants (FIG. 4A and 6) and to the cytokinin, $N_6$-(2-isopentenyl) adenine (2IP) (FIG. 4B-1, B-2, B-3). These results had not been observed previously and in fact, the prior art actually teaches away from this finding suggesting that over-expression of plant AtPGP-1 is not involved in drug resistance. See Sidler, M. et al., 1998, *The Plant Cell* 10:1623–1636. Therefore, this result was particularly unexpected in plants. Additionally, since Arabidopsis plants overexpressing AtPGP-1 are able to grow in both cycloheximide and cytokinin, this suggests that the conference of drug resistance by AtPGP-1 is likely to be seen with other chemicals as well and is not an isolated phenomenon.

Figure 6:
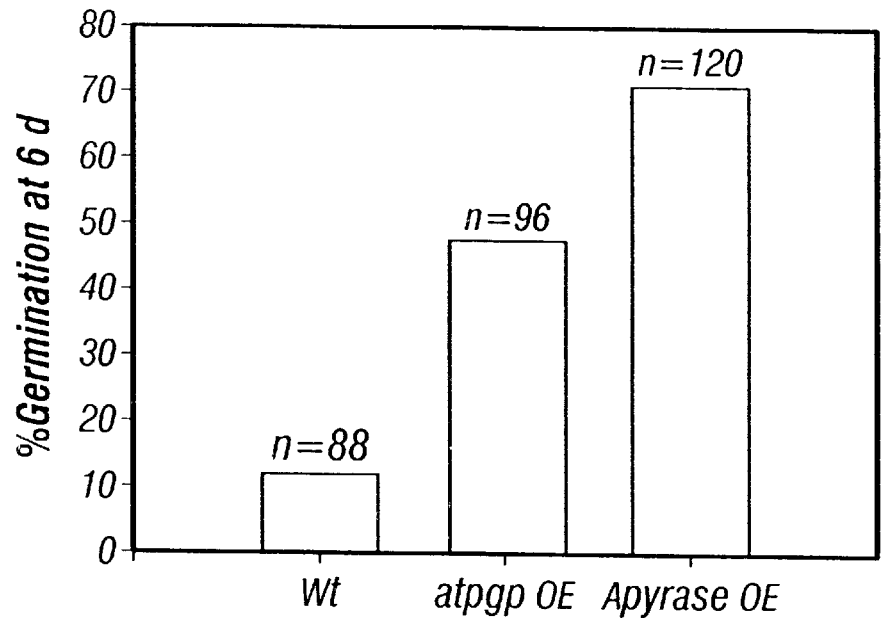
FIG. 6. Graph showing germination rate of Arabidopsis plants grown in the presence of cycloheximide which overexpress either the ecto-phosphatase, apyrase, or the ABC transporter AtPGP-1.

Effect of over-expression of apyrase on drug resistance in plants: Another unexpected result was obtained when the plant apyrase gene was over-expressed in plants. Overexpression of apyrase in plants resulted in the conference of resistance to cycloheximide (FIGS. 4A and 6). The same result was obtained when the plants were grown in the presence of a cytokinin, $N_6$-(2-isopentenyl) adenine (FIG. 4B-1, B-2, B-3). In fact, over-expression of apyrase is surprisingly able to raise the germination rate above the level obtained by the over-expression of the MDR gene AtPGP-1 (FIGS. 4A, 4B-1, 4B-2, 4B-3 and 6). Just as under-expression of phosphatase activity in a yeast mutant lacking two potent extracellular phosphatases diminished its resistance to cycloheximide (FIG. 3A), over-expression of a powerful extracellular ATP phosphatase in plants bolstered resistance. The fact that higher resistance was found in plants genetically manipulated only with respect to phosphatase: over-expression and not MDR1, indicates that there likely exists other ATP-symporters used in detoxification in addition to MDR1. Minimally, the stronger ATP gradient set up by apyrase in the transgenic plants affects the kinetics of the wild-type MDR1.

EXAMPLE 3
ATP Efflux in Yeast and Plants Overexpressing AtPGP-1
Materials and Methods ATP collection: Yeast cells used in the luciferase assays were grown for two days and then transferred to fresh media at the time of the assay. From this time forward, the cells were kept at room temperature on a rotator. Every hour a 1 ml aliquot was taken, the cells in the aliquot were counted on a hemocytometer, a methylene blue viability assay was performed (Boyum, R. and Guidotti, G., 1997, *Microbiology* 143:1901–1908), the cells were centrifuged, and the supernatant was stored in liquid nitrogen until all the aliquots were collected. For luciferase assays involving plants, *Arabidopsis thaliana* plants were grown in sterile culture at 22° C. under 150–200 $\mu E$ of continuous light for at least 15 days. Foliar ATP was collected by placing a single 30 $\mu l$ drop of luciferase buffer (Analytical Luminescence Laboratory, Cockeysville, Md.) on a leaf and, without making direct physical contact with the plant, the droplet was immediately collected and snap frozen. For each leaf, the area was approximated as an integrated area of a 2-D image of the leaf using NIH1.52 software (Shareware, NIH).

Luminometry: Samples were reconstituted to a 100 $\mu l$ final volume in Firelight™ buffer (Analytical Luminescence Laboratory, Cockeysville, Md.). After the buffer was added, all samples were kept on ice. ATP standards were reconstituted in 100 $\mu l$ of Firelight™ buffer and the standards and sample were loaded into a 96-well plate and read on an automated Dynex Technologies Model MLX luminometer (Dynex Technologies, Chantilly, Va.). Samples were processed with the addition of 50 $\mu l$ of Firelight™ enzyme (Analytical Luminescence Laboratory, Cockeysville, Md.) followed by a reading delay of 1.0 second and an integration time of 10 seconds. Output was taken as an average for the integration time and then averaged for multiple samples. The sample handling time was less than 2 hours.

Pulse Chase experiments: Yeast were grown to saturation in liquid medium, as described above, centrifuged, and resuspended in fresh medium containing 1 $\mu Ci/ml$ $^3H$-adenosine (Amersham, Arlington Heights, Ill.). The cells were rotated at room temperature for 20 minutes to allow adenosine uptake. After 20 minutes the cells were centrifuged. The pellet was washed twice in ice cold medium, resuspended in culture medium at room temperature, divided equally between five types (five per cell line), and placed on a rotator. Every ten minutes a separate tube from each cell line was centrifuged and the pellet and supernatant were placed in separate scintillation vials. The efflux activity was expressed as the ratio of counts in the supernatant to counts in the pellet.

Results

Figure 7:
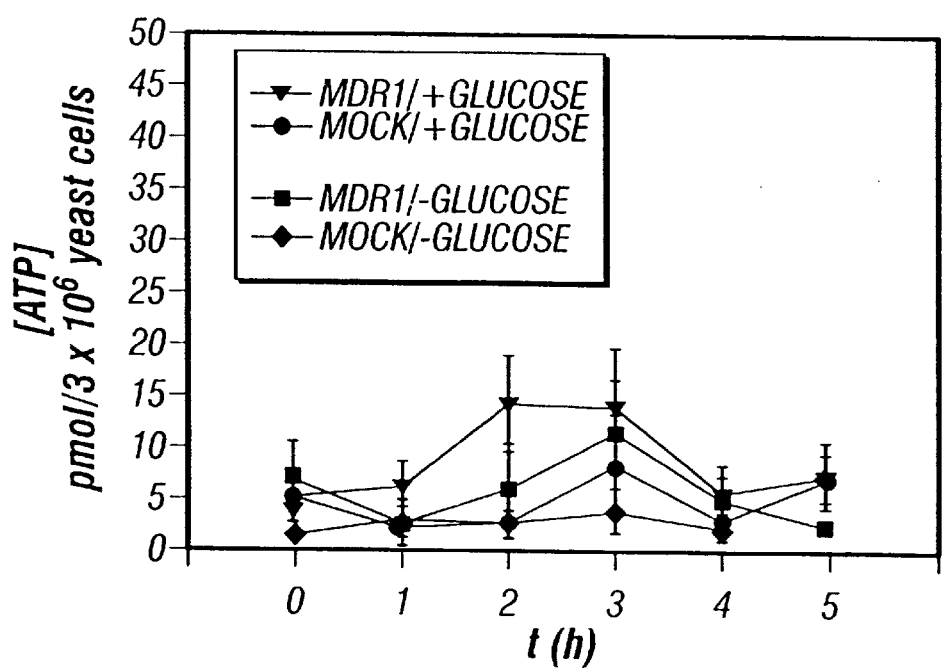
FIG. 7. Graph of steady-state levels of ATP in the extracellular fluid of wild-type yeast cells grown in the presence or absence of glucose and in the presence or absence of over-expression of the Arabidopsis plant ABC transporter, AtPGP-1.
Figure 8:
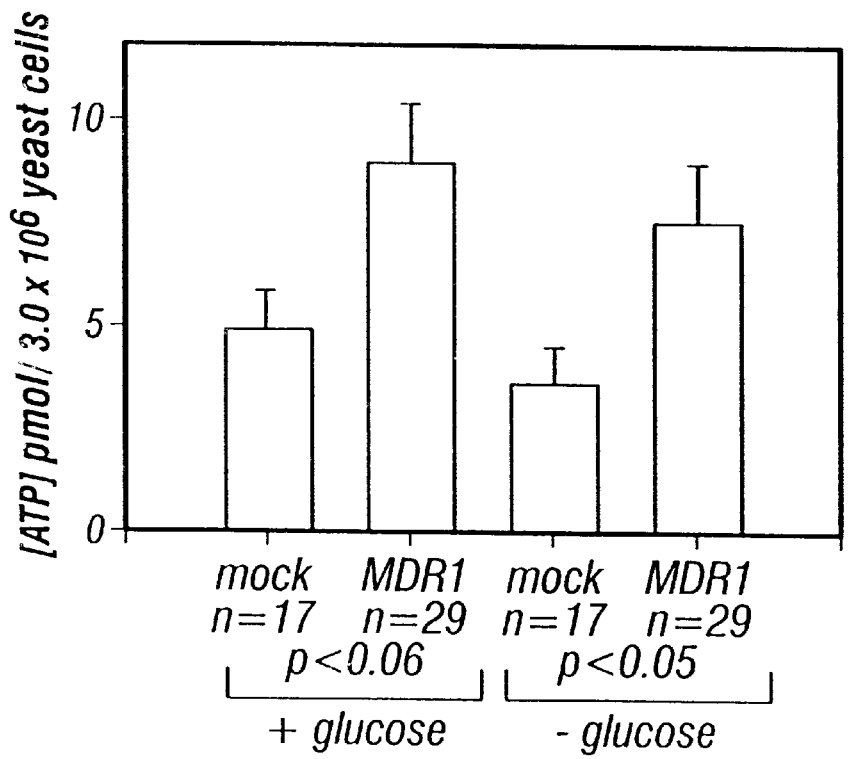
FIG. 8. Graph showing that over-expression of Arabidopsis plant ABC transporter, AtPGP-1, in yeast can double the steady-state levels of ATP in the extracellular fluid.
Figure 9:
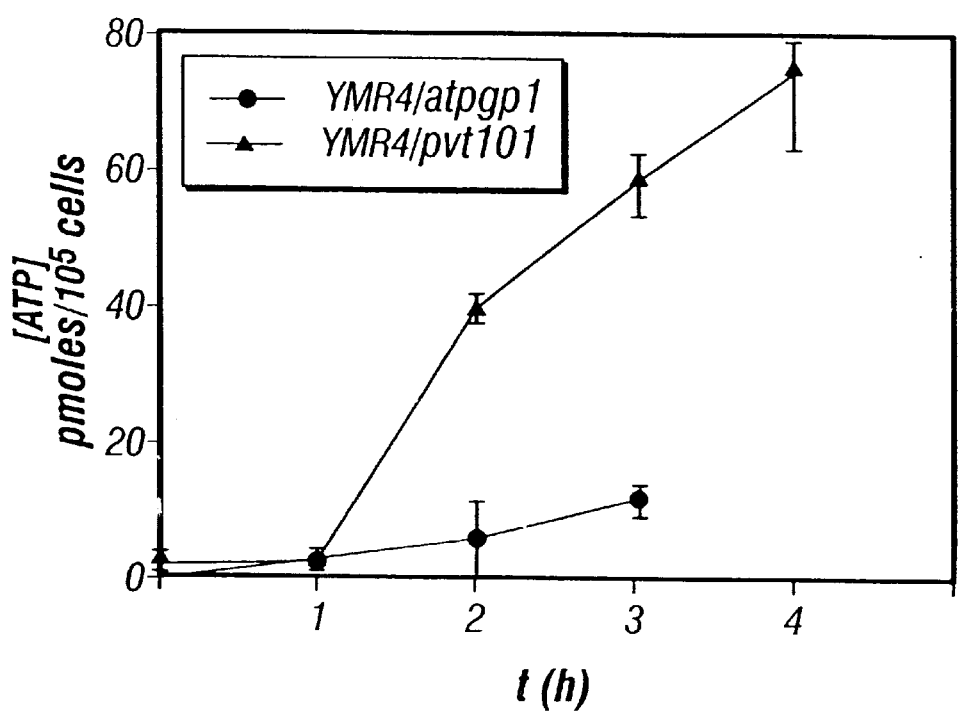
FIG. 9. Graph showing that a yeast mutant, YMR4, that has a deficient ecto-phosphatase, accumulates ATP in the extracellular fluid and the over-expression of AtPGP-1 increases the accumulation of ATP.
Figure 10:
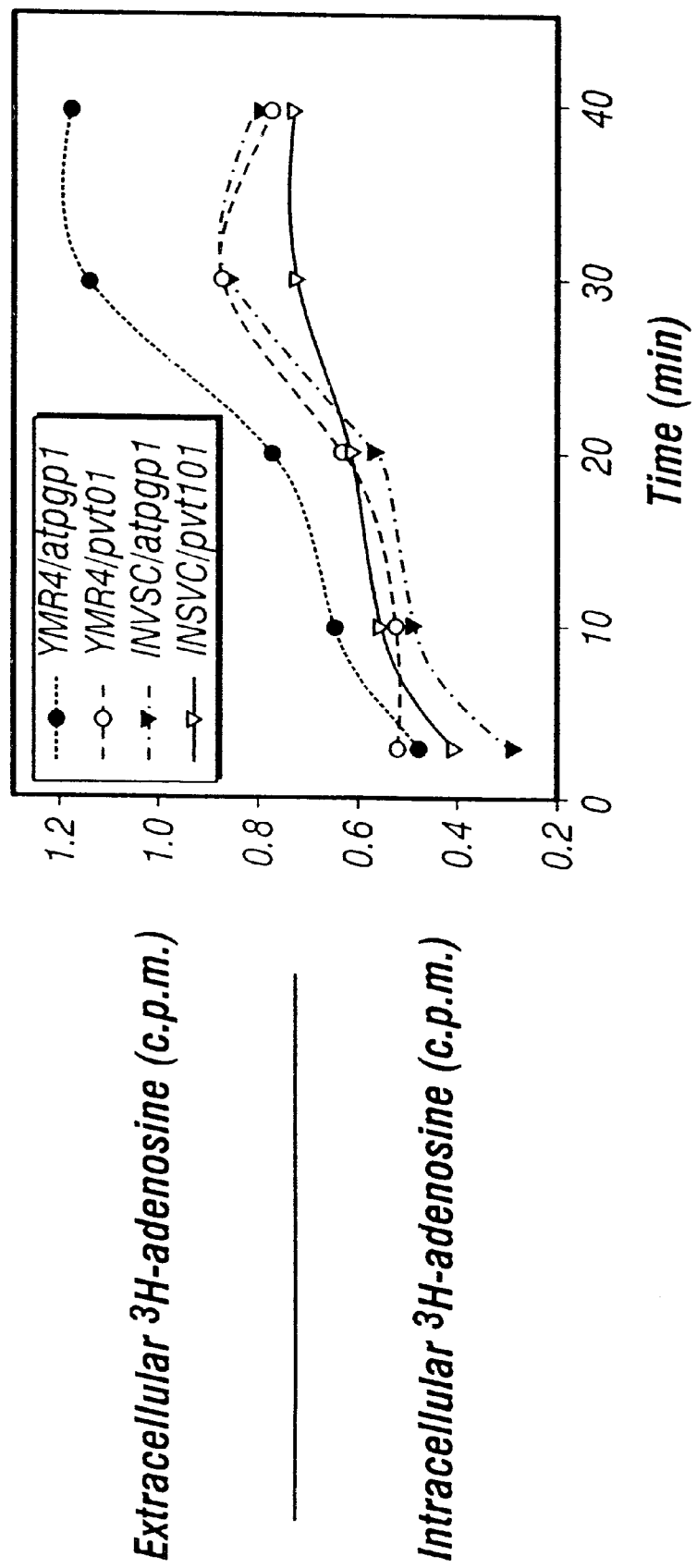
FIG. 10. Graph showing results of a pulse-chase experiment in either wild-type yeast cells or a yeast mutant, YMR4, which is deficient in ecto-phosphatase activity, in the presence and absence of over-expression of Arabidopsis plant ABC transporter, AtPGP-1, demonstrating an early differential ATP efflux of cells over-expressing AtPGP-1.
Figure 11:
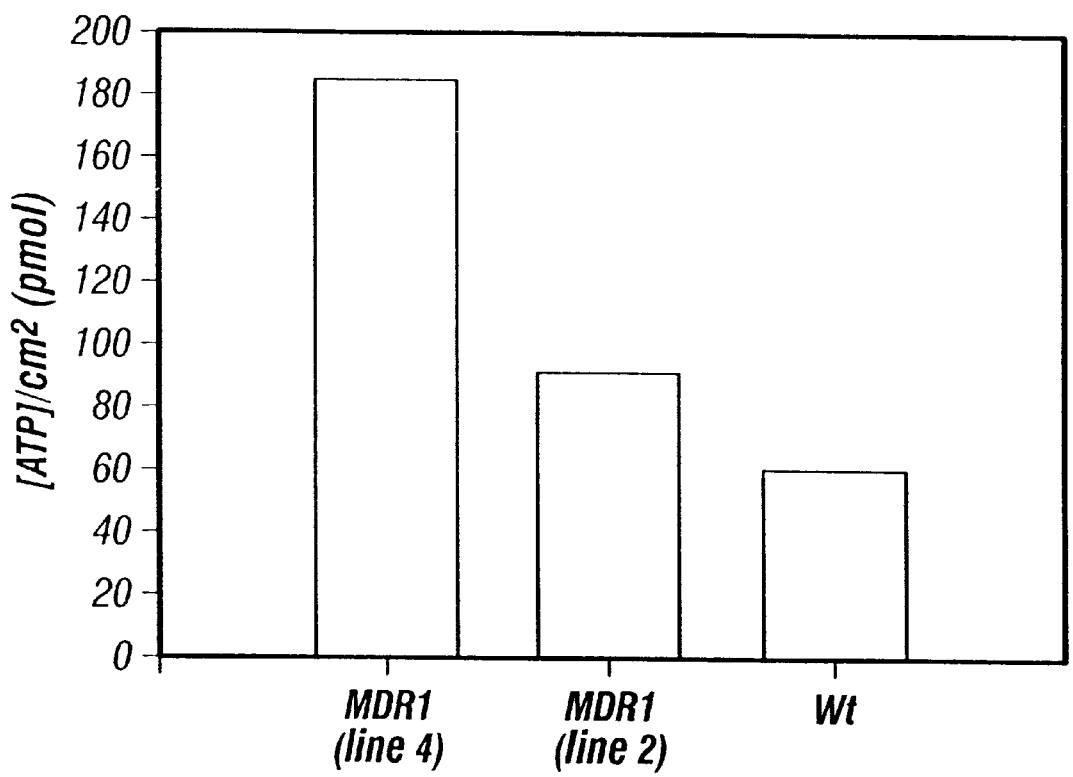
FIG. 11. Graph of ATP levels on the surface of leaves of Arabidopsis plants over-expressing AtPGP-1 (MDR1).

The ATP effluxed by the plant MDR1, AtPGP-1, over-expressed in veast: In wild-type cells there is a steady-state level of ATP in the extracellular fluid, which is to say that the ATP outside the cells is rapidly degraded by phosphatases and does not accumulate over time (FIG. 7). However, the expression of the AtPGP-1 doubled this steady-state level (FIG. 8). If the yeast mutant, YMR4, which is deficient in extracellular phosphatase activity, is analyzed, there was a noticeable accumulation of ATP in the extracellular fluid compared to a control mutant transformed with empty plasmid pVT101 (FIG. 9). In addition to ATP measurements based on luminometry performed on a kinetic time-scale of hours, an earlier differential ATP efflux in MDR1 expressing cell s by pulse chase experiments was demonstrated (FIG. 10). Furthermore, *Arabidopsis thaliana* plants from two independently transformed lines, that constitutively express the AtPGP-1 protein, showed a significant accumulation of ATP on their leaf surfaces (FIG. 11). Taken together, these data demonstrate the absolute ability of plant MDRI, AtPGP-1, to transport ATP from inside the cell to the outside. Moreover, these data show that ATP efflux channels and phosphatases both have roles in the steady-state level of ATP outside of the cell. This is the first demonstration of the importance of extracellular ATP steady-state levels, and the importance of an ATP gradient across biological membranes in the modulation of drug resistance.

EXAMPLE 4
A Two-Component System is Found in Arabidopsis Plants
Materials and Methods Plant Growth: Arabidopsis seeds were sown in a solid germination media containing MS salts (Sigma Chemical, St. Louis, Mo.), 2% sucrose, 0.8% agar, and vitamins (Valvekens, D. et al., 1992, *Proc. Natl. Acad. Sci. USA* 85:5536–5540). For selection assays, one of the following, or a combination of both, Was added to media (cooled to less than 50° C. before adding) immediately prior to pouring into plates: cycloheximide at a final concentration of 500 ng/ml; α,β-methyleneadenosine 5'-diphosphate at a final concentration of 1 mM. Plant growth was measured by germination percentage after 10–20 days.

All other materials and methods were discussed above in Example 2.

Results

Figure 12:
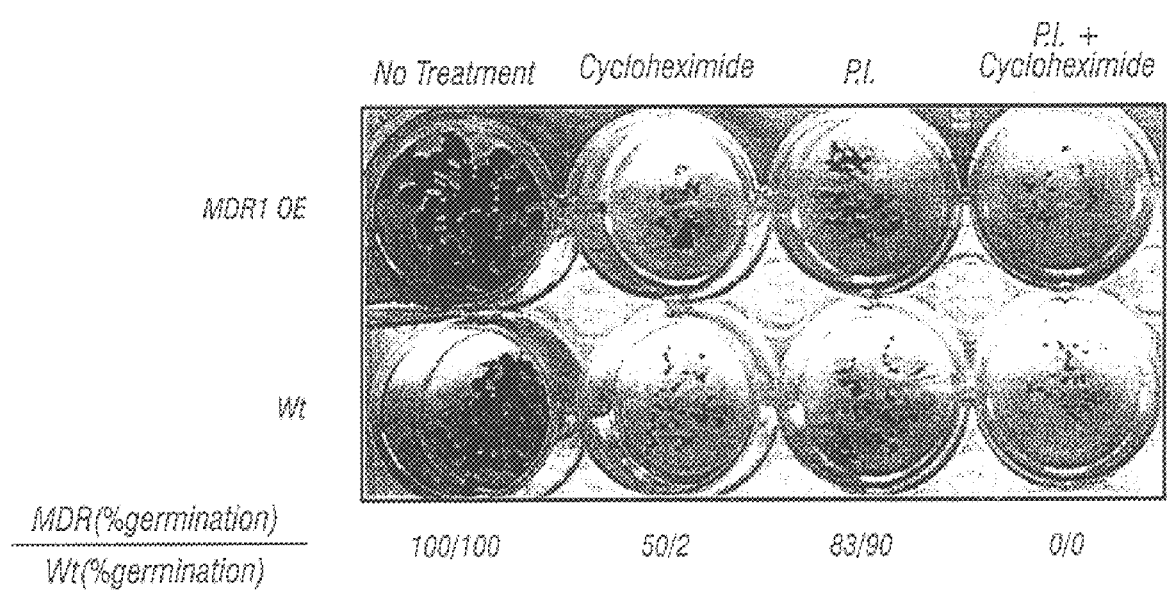
FIG. 12. Effects of phosphatase inhibitor in wild-type and AtPGP-1 (MDR1) overexpressing Arabidopsis plants.

Effects of phosphatase inhibitor on plants overexpressing AtPGP-1: FIG. 12 shows that when wild-type and AtPGP-1 overexpressing (MDR OE) *Arabidopsis thaliana* plants were either treated with nothing (lane 1), cycloheximide (lane 2), α,β-methyleneadenosine 5'-diphosphate (phosphatase inhibitor) (lane 3), or cycloheximide and phosphatase inhibitor (lane 4), both the wild-type and the AtPGP-1 overexpressing plants were affected similarly by the presence of phosphatase inhibitor. While the AtPGP-1 overexpressing plants grew significantly better in the presence of cycloheximide alone with a 50% germination rate for the AtPGP-1 overexpressing plants and a 2% germination rate for the wild-type plants, similar germination rates were seen for both the AtPGP-1 overexpressing and wild-type plants in the presence of either phosphatase inhibitor alone (83% and 90% germination respectively) or cycloheximide plus phosphatase inhibitor (no germination at all). The addition of phosphatase inhibitor surprisingly destroys the ability of the AtPGP-expressing plants to grow in the presence of cycloheximide. These data suggest that phosphatases are involved in the conference of drug resistance in plants and that there is a two-component system similar to that demonstrated in yeast in Example 2 and 3 above in which an MDR-like protein and an ATP-gradient-maintaining ecto-phosphatase are important in modulating drug resistance.

EXAMPLE 5

THE ATP Gradient Directly Effects Drug Resistance in Cells

Materials and Methods

Cell lines: Cell lines were the same as those described above in Example 2 and 3. YMR4 MDR1 is the phosphatase mutant yeast strain overexpressing AtPGP-1; YMR4 pVT101 contains vector alone; INVSC MDR1 is the wild-type yeast strain overexpressing AtPGP-1; and INVSC pVT101 contains vector alone.

Selection in drug: To create drug resistant yeast strains, all four cell lines were grown up in the presence of 500 ng/ml of cycloheximide, and transferred to other cycloheximide containing plates after a period of four to six days. This transfer of cell lines and subculturing continued such that the yeast cells grew in the presence of cycloheximide for a period of at least a month.

Cells cultured in media alone: To create cell lines that had not been preselected for their ability to grow in drug, yeast strains were grown on plates containing YNB (Bio101, Vista, Calif.) without uracil (-URA) to maintain the presence of the vector (which supplies URA) without any drugs added.

Growth of cells in suspension for ATP and drug selection experiments: Cells were transferred into 5 ml YNB-URA liquid media for turbidity measurements. All cell lines (both non-drug selected and drug-selected) were grown in media with the addition of either nothing, 500 ng/ml cycloheximide, 100 mM ATP, or 500 ng/ml cycloheximide and 100 mM ATP. Turbidity readings were taken after 48 hours.

Growth of cell lines in suspension for salvage pathway experiments: All cell lines were grown in liquid media either containing drug (for the drug selected lines) or not containing drug (for the non-drug selected lines). When the cultures reached a turbidity of 1.00 as measured at a wavelength of 600 in a spectrophotometer ($OD_{600}$=1.00), 10 μl of each culture was then removed and placed in either media with nothing added, 3 mM potassium phosphate; 3 mM adenosine; 9 mM potassium phosphate and 3 mM adenosine (for controls); potassium phosphate and cycloheximide; adenosine and cycloheximide; adenosine, cycloheximide, and potassium phosphate. Cell cultures were further grown for 72 hours, and their turbidity was determined by $OD_{600}$ readings on a spectrophotometer.

Growth of cell lines for nigericin experiments: Drug selected lines were removed from cycloheximide containing plates and placed in 5 ml liquid media containing 5 ng/ml cycloheximide. Cell cultures were allowed to grow until they reached an $OD_{600}$ reading of 1.00, and then 10 μl from each culture was removed and transferred to culture tubes containing 5 ml of liquid media and 25 μg/ml nigericin. $OD_{600}$ readings were recorded daily for a period of up to 72 hours to determine growth.

Results

An ATP gradient is critical in MDR: The importance of the ATP gradient in MDR in yeast cells was demonstrated by showing that the growth of cells which were previously grown in drug and had developed resistance to the drug, were not able to grow in high levels of ATP unless they were overexpressing AtPGP-1 (FIG. 13). Cells which had not been previously selected in drug were able to grow in the presence of high levels of ATP (FIG. 13). These data emphasize that the loss of an ATP gradient is previously resistant cell lines abolishes resistance. This result is new to the understanding of MDR and has led to vast insight into the understanding of the mechanism by which MDR-ABC transporters confer resistance to cells and to methods to modulate such resistance. Moreover, when cells were grown in high levels of ATP and drug (cycloheximide), even the cell lines which had previously showed resistance to drug were unable to grow in the presence of drug and ATP. These data indicate that when the ATP gradient across biological membranes is destroyed (by the presence of high extracellular levels of ATP), efflux of drugs cannot be achieved and therefore, drug resistance is abolished. In summary, the multi-drug resistance channel is not functional without an ATP gradient.

The drug resistance is not due to an adenosine salvage pathway: In order to address whether the involvement of a nucleotide salvage pathway was responsible for the results of the present invention, yeast cells were cultured in the presence of extracellular adenosine and extracellular phosphate. The acid phosphatase yeast mutant, YMR4, was selected because its decreased ecto-phosphatase activity makes it an ideal candidate for studying the effect of extracellular nucleotides on growth. If an adenosine salvage pathway were involved, then the presence of extracellular adenosine or possibly phosphate should help cells recoup the intracellular ATP losses due to ATP/drug efflux and should help cells grow in the presence of drug whether or not the cells were overexpressing AtPGP-1. In contrast, however, the addition of adenosine or phosphate to the media did not enhance resistance to the cells (FIG. 14). In fact, cells overexpressing AtPGP-1 grew best in drug alone, with the addition of adenosine and/or phosphate being slightly inhibitory. Furthermore, cells which did not express AtPGP-1 were unable to grow in drug regardless of the presence of adenosine and/or phosphate. These data suggest that an adenosine salvage pathway is not the principal mechanism at work in the present invention.

What is claimed is:

1. A transgenic plant or a progeny thereof comprising a plurality of plant cells transformed with one or more nucleotide sequences encoding polypeptides selected from a group consisting of *Pisum sativum* apyrase and *Homo sapiens* apyrase, wherein the polypeptides are further defined as comprising the sequence in GenBank accession # Z32743, AF034840, AF039916, AF039917, AF039918, and/or HSUS87967.

2. The transgenic plant of claim 1, wherein the polypeptide is further defined as *Pisum sativum* apyrase having a sequence in GenBank accession # Z32743.

3. The transgenic plant of claim 1, wherein the polypeptide is further defined as *Homo sapiens* apyrase having a sequence in GenBank accession # AF034840, AF039916, AF039917, AF039918 and/or HSU87967.

4. A plant transformation vector comprising a polynucleotide encoding one or more polypeptides selected from the group consisting of *Pisum sativum* apyrase and *Homo sapiens* apyrase and a plant-functional promoter operatively linked to said polynucleotide wherein the polypeptides are further defined as comprising the sequence in GenBank accession #Z32743, AF034840, AF039916, AF039917, AF039918, and/or HSUS87967.

5. The transformation vector of claim 4, wherein the polypeptide is further defined as *Pisum sativum* apyrase having a sequence in GenBank accession# Z32743.

6. The transformation vector of claim 4, wherein the polypeptide is further defined as *Homo sapiens* apyrase having a sequence in GenBank accession # AF034840, AF039916, AF039917, AF039918 and/or HSU87967.

7. A method for enhancing an ATP gradient across a biological membrane of a plant cell by causing or increasing expression of an AtPGP-1 by introduction of a nucleic acid sequence encoding an AtPGP-1 to the cell or a progenitor of the plant cell, wherein the nucleic acid sequence encoding an AtPGP-1 is further defined as a nucleic acid encoding *Arabidopsis thaliana* AtPGP-1 comprising the sequence in Genbank accession # X61370.

8. A method of conferring plant hormone resistance to a plant cell comprising causing or increasing expression of an ectophosphatase that has ATPase activity in the plant cell by introduction of a nucleic acid sequence encoding an ectophosphatase that has ATPase activity in the plant cell to the plant cell or a progenitor of the plant cell, wherein expression of said ectophosphatase stimulates efflux of said hormone from said cell, wherein said ectophosphatase is selected from the group consisting of *Pisum sativum* apyrase and *Homo sapiens* apyrase, wherein the ectophosphatase is further defined as comprising the sequence in GenBank accession # Z32743, AF034840, AF039916, AF039917, AF039918, and/or HSUS87967.

9. The method of claim 8, wherein the ectophosphatase is further defined as *Pisum sativum* apyrase having a sequence in GenBank accession # Z32743.

10. The method of claim 8, wherein the ectophosphatase is further defined as *Homo sapiens* apyrase having a sequence in GenBank accession # AF034840, AF039916, AF039917, AF039918 and/or HSU87967.

11. A plant hormone resistant plant cell produced by the method of claim 8.

12. The cell of claim 11, further defined as being comprised in a plant.

13. A method of conferring herbicide resistance to a plant cell comprising causing or increasing expression of an ectophosphatase that has ATPase activity in the plant cell by introduction of a nucleic acid sequence encoding an ectophosphatase that has ATPase activity in the plant cell to the plant cell or a progenitor of the plant cell, wherein expression of said ectophosphatase stimulates efflux of said herbicide from said cell, wherein said ectophosphatase is selected from the group consisting of *Pisum sativum* apyrase and *Homo sapiens* apyrase, wherein the ectophosphatase is further defined as comprising the sequence in GenBank accession # Z32743, AF034840, AF039916, AF039917, AF039918, and/or HSUS87967.

14. The method of claim 13, wherein the ectophosphatase is further defined as *Pisum sativum* apyrase having a sequence in GenBank accession # Z32743.

15. The method of claim 13, wherein the ectophosphatase is further defined as *Homo sapiens* apyrase having a sequence in GenBank accession # AF034840, AF039916, AF039917, AF039918, and/or HSU87967.

16. A herbicide resistant plant cell produced by the method of claim 13.

17. The plant cell of claim 16, further defined as being comprised in a plant.

18. A method for altering the ATP gradient across the biological membrane of a plant cell by causing or increasing expression of an ectophosphatase that has ATPase activity in the plant cell by introduction of a nucleic acid sequence encoding an ectophosphatase that has ATPase activity in the plant cell to the plant cell or a progenitor of the plant cell, wherein said ectophosphatase is selected from the group consisting of *Pisum sativum* apyrase and *Homo sapiens* apyrase, wherein the ectophosphatase is further defined as comprising the sequence in GenBank accession # Z32743, AF034840, AF039916, AF039917, AF039918, and/or HSUS87967.

19. The method of claim 18, wherein the ectophosphatase is further defined as *Pisum sativum* apyrase having a sequence in GenBank accession # Z32743.

20. The method of claim 18, wherein the ectophosphatase is further defined as *Homo sapiens* apyrase having a sequence in GenBank accession # AF034840, AF039916, AF039917, AF039918 and/or HSU87967.

\* \* \* \* \*

UNITED STATES PATENT AND TRADEMARK OFFICE
CERTIFICATE OF CORRECTION

PATENT NO.       : 6,448,472 B1                                                    Page 1 of 1
APPLICATION NO.  : 09/244791
DATED            : September 10, 2002
INVENTOR(S)      : Collin E. Thomas et al.

It is certified that error appears in the above-identified patent and that said Letters Patent is hereby corrected as shown below:

In column 1, lines 7-9, delete
"The present invention involves subject matter developed under NSF Grant Numbered IBN9603884, so that the United States Government may have certain rights herein."
and insert
--This invention was made with government support under Grant No. IBN9603884 awarded by the National Science Foundation. The government has certain rights in the invention.-- therefor.

Signed and Sealed this

Twenty-seventh Day of April, 2010

David J. Kappos
*Director of the United States Patent and Trademark Office*